United States Patent
Fang et al.

(10) Patent No.: US 12,421,246 B2
(45) Date of Patent: Sep. 23, 2025

(54) METHOD FOR SYNTHESIS OF DIAZABICYCLO[6.2.0]DECANE RELATED COMPOUNDS

(71) Applicant: Eisai R&D Management Co., Ltd., Tokyo (JP)

(72) Inventors: Francis G. Fang, Andover, MA (US); Branko Mitasev, North Reading, MA (US); Jiong Yang, Andover, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 1052 days.

(21) Appl. No.: 17/421,922

(22) PCT Filed: Jan. 9, 2020

(86) PCT No.: PCT/US2020/012839
§ 371 (c)(1),
(2) Date: Jul. 9, 2021

(87) PCT Pub. No.: WO2020/146568
PCT Pub. Date: Jul. 16, 2020

(65) Prior Publication Data
US 2022/0112207 A1    Apr. 14, 2022

Related U.S. Application Data

(60) Provisional application No. 62/790,340, filed on Jan. 9, 2019.

(51) Int. Cl.
| | | |
|---|---|---|
| C07D 487/04 | (2006.01) | |
| C07C 229/36 | (2006.01) | |
| C07C 247/10 | (2006.01) | |
| C07C 311/18 | (2006.01) | |
| C07D 203/12 | (2006.01) | |
| C07D 205/04 | (2006.01) | |
| C07D 307/33 | (2006.01) | |
| C07D 317/28 | (2006.01) | |
| C07D 403/06 | (2006.01) | |
| C07D 405/14 | (2006.01) | |
| C07D 491/147 | (2006.01) | |

(52) U.S. Cl.
CPC ........ *C07D 491/147* (2013.01); *C07C 311/18* (2013.01); *C07D 307/33* (2013.01); *C07D 403/06* (2013.01); *C07D 405/14* (2013.01); *C07D 487/04* (2013.01)

(58) Field of Classification Search
CPC ........................ C07D 487/04; C07D 491/147; C07D 203/12; C07D 205/04; C07D 307/33; C07D 317/28; C07C 229/36; C07C 247/10
See application file for complete search history.

(56) References Cited

U.S. PATENT DOCUMENTS

2016/0289235 A1    10/2016    Comer et al.

FOREIGN PATENT DOCUMENTS

| | | |
|---|---|---|
| CN | 101962350 A | 2/2011 |
| JP | 2017502080 A | 1/2017 |
| WO | 2015070204 A1 | 5/2015 |
| WO | 2018175385 A1 | 9/2018 |

OTHER PUBLICATIONS

Liu et al. (Chemical Communications (Cambridge, United Kingdom) (2010), 46(44), 8460-8462).*
International Search Report (PCT/ISA/210) and Written Opinion (PCT/ISA/237) mailed on Jun. 30, 2020, by the U.S. Patent and Trademark Office as the International Searching Authority for International Application No. PCT/US2020/012839.
Lowe, Jason T., et al., "Synthesis and Profiling of a Diverse Collection of Azetidine-Based Scaffolds for the Development of CNS-Focused Lead-like Libraries", Journal of Organic Chemistry,vol. 77, No. 17, Sep. 7, 2012 (Sep. 7, 2012), pp. 7187-7211.
Office Action (Notice of Reasons for Rejection) issued on Jan. 9, 2024, by the Japanese Patent Office in corresponding Japanese Patent Application No. 2021-540181, and an English Translation of the Office Action. (8 pages).
Office Action (Notification of the First Office Action) issued on Feb. 29, 2024, by the China National Intellectual Property Administration in corresponding Chinese Patent Application No. 202080017679. 9, and an English Translation of the Office Action. (23 pages).

* cited by examiner

*Primary Examiner* — Bruck Kifle
(74) *Attorney, Agent, or Firm* — Buchanan Ingersoll & Rooney PC

(57) ABSTRACT

A method for the synthesis of diazabicyclo[6.2.0]decane compounds is provided. The synthesis proceeds by stereoselective synthesis of a chiral lactone followed by azetidine formation via a series of chemoselective reactions. Bicyclization results with the formation of diazobicyclo[6.2.0] decane related compounds.

46 Claims, 2 Drawing Sheets

METHOD FOR SYNTHESIS OF DIAZABICYCLO[6.2.0]DECANE RELATED COMPOUNDS

CROSS-REFERENCE TO RELATED APPLICATIONS

This application is the United States national stage under 35 U.S.C. Section 371 of PCT International Patent Application No. PCT/US2020/012839, which was filed on Jan. 9, 2020, and which claims the benefit of U.S. Provisional Patent App. No. 62/790,340, filed on Jan. 9, 2019, which is incorporated by reference herein.

STATEMENT OF GOVERNMENT SUPPORT

This invention was made with government support under Award Numbers W81XWH-16-1-0719 and W81XWH1810294, both awarded by the United States Department of Defense under the Peer Reviewed Medical Research Program. The government has certain rights in the invention.

FIELD

The present invention relates to stereochemically defined syntheses for producing 1,6-diazabicyclo[6.2.0]decanes.

BACKGROUND

Malaria is an infectious disease caused by protozoan parasites of the genus *Plasmodium*. The eradication of malaria has been difficult due to the complex life cycle of *Plasmodium* and the emergence of parasite resistance. Diversity-oriented synthesis (DOS) has been used to identify antimalarial compounds. For example, phenylalanyl-tRNA synthetase inhibitor BRD7929 has been identified. BRD7929 exhibits activity in all stages of the parasite life cycle.

BRD7929, which has the chemical name (8R,9S,10S)-10-[(dimethylamino)methyl]-N-(4-methoxyphenyl)-9-[4-(2-phenylethynyl)phenyl]-1,6-diazabicyclo[6.2.0]decane-6-carboxamide, is reported in United States Patent Application Publication No. US2016/0289235, which is incorporated by reference herein. BRD7929 has the following structure:

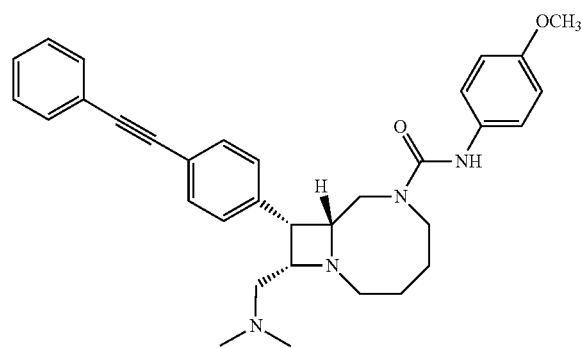 [SMILES: COc1ccc(NC(=O)N2CCCCN3[C@H](CN(C)C)[C@H](c4ccc(C#Cc5ccccc5)cc4)[C@@H]3C2)cc1]

Likewise, the compound given by the following structure (Formula XIV, or compound 22) has also been identified as useful in the treatment and/or prophylaxis of diseases spread by parasites, including malaria and cryptosporidiosis:

(Formula XIV, Compound 22)

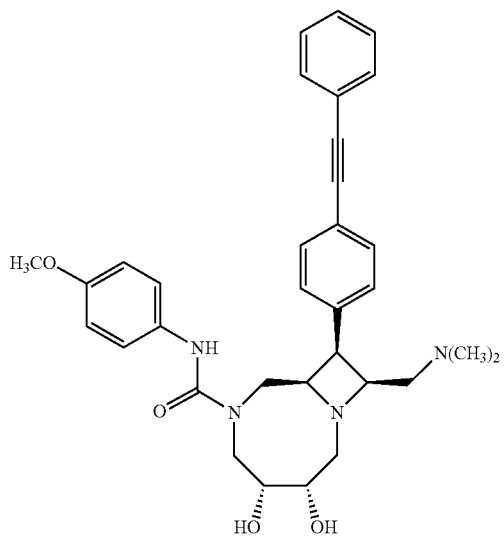

See WO 2018/175385, which is relied upon and incorporated herein in its entirety.

Additional related compounds also described as useful in therapies to combat diseases spread by parasites (including, for example, malaria and cryptosporidiosis) and their syntheses may be found in WO 2018/175385; Lowe, J. T. et al. Synthesis and profiling of a diverse collection of azetidine-based scaffolds for the development of CNS-focused lead-like libraries, J. Org. Chem. 77, 7187-7211 (2012); Maetani, M. et al. Synthesis of a Bicyclic Azetidine with In Vivo Antimalarial Activity Enabled by Stereospecific, Directed C(sp$^3$)-H Arylation, J.A.C.S. 139, 11300-11306 (2017); and Kato, N. et al. Diversity-oriented synthesis yields novel multistage antimalarial inhibitors, Nature 538, 344-349 (2016); all of which are relied upon and incorporated herein in their entirety.

Additional references relevant to the preparation of compounds for and treatment of parasitic diseases include the following: WO 2015070204, WO 2015002755, WO 2016172631, and US 2018/0194768; all of which are relied upon and incorporated by reference herein in their entirety.

However, a lengthy, low-yielding and/or costly synthetic route limits the usefulness of this compound. While BRD7929, Formula XIV and related compounds are known to have therapeutic value, improved synthetic routes to their production could simultaneously afford further medicinal chemistry exploration of this class of compounds and reduce their cost of production thereby making development and/or widespread delivery of these therapeutics more feasible. Thus, there is a need for improved syntheses for making these potential antimalarial compounds.

BRIEF SUMMARY

One embodiment is directed to a method of forming a solid compound given by Formula I:

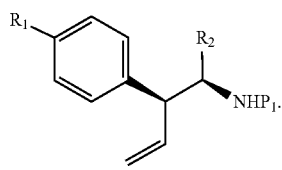
(Formula I)

In Formula I, $R_1$ is —I, —Cl, —Br, or

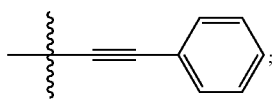;

$R_2$ is $C(O)R_3$; $R_3$ is —O⁻; and a positive counterion is ionically associated with Formula I; and $P_1$ is a nitrogen protecting group. The method includes reacting a reactant of Formula II

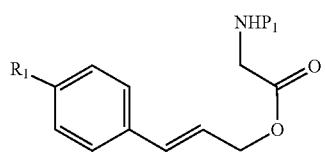
(Formula II)

with a base and resolving the racemic mixture by crystallization with a chiral reagent.

In one embodiment, $R_1$ is

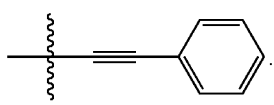.

In another embodiment, $P_1$ is selected from a group that consists of consisting of —C(O)CF$_3$, —C(O)OC(CH$_3$)$_3$, and —C(O)OCH$_2$Ph.

In another embodiment, $P_1$ is —C(O)CF$_3$.

In another embodiment, the reacting base is lithium diisopropyl amine and is in the presence of ZnCl$_2$.

In another embodiment, the chiral reagent is (R)-(+)-1-phenylethylamine.

In another embodiment of forming a compound given by Formula I, $R_1$ is —I, —Cl, —Br, or

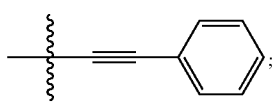;

$R_2$ is $C(O)R_3$; $R_3$ is —Oalkyl; and $P_1$ is a nitrogen protecting group. The method includes reacting a reactant of Formula III

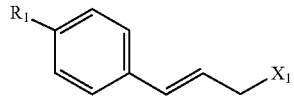
(Formula III)

with a chiral sulfinyl imine, wherein $X_1$ is a halogen atom.

In one embodiment, $R_1$ and $X_1$ are each —Br, and the chiral sulfinyl imine is

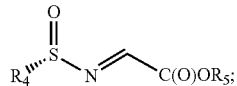;

$R_4$ and $R_5$ are linear or branched alkyl.

In another embodiment, $R_4$ is —C(CH$_3$)$_3$ and $R_5$ is —CH$_2$CH$_3$.

In another embodiment, the reacting is in the presence of Zn.

Another embodiment may be directed to a method of forming a compound given by Formula IV:

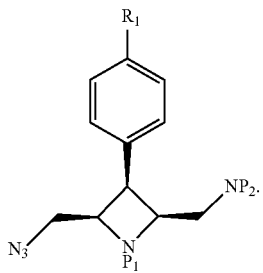
(Formula IV)

In Formula IV, $R_1$ is —I, —Cl, —Br, or

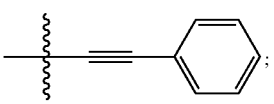;

$P_1$ and $P_2$ are the same or different and represent nitrogen protecting groups. The method includes forming a lactone of Formula V:

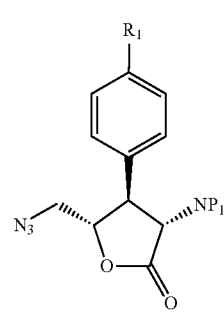
(Formula V)

from a compound of Formula I

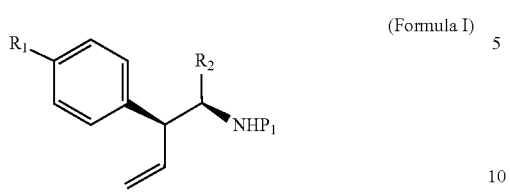
(Formula I)

wherein R₂ is C(O)R₃; R₃ is —OH, —Oalkyl, —O⁻; and when R₃ is —O⁻, a positive counterion is ionically associated with Formula I; and P₁ is a nitrogen protecting group; reducing the lactone of Formula V into a compound of Formula VI:

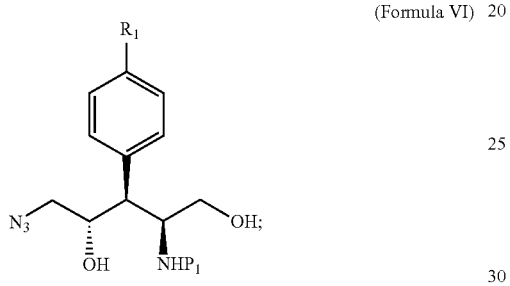
(Formula VI)

and converting the alcoholic groups covalently attached to the unsaturated carbons of Formula VI into leaving groups to form an intermediate that reacts with a nitrogen nucleophile to generate a compound of Formula IV.

In one embodiment, the nitrogen nucleophile is phthalimide.

In another embodiment, R₁ is

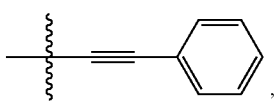

R₂ is —C(O)O⁻, and P₁ is —C(O)CF₃.

In another embodiment, the lactone of Formula V is formed by reacting the compound of Formula I with an electropositive source of a halogen in a polar solvent.

In another embodiment, electropositive source of a halogen is I₂ and the polar solvent is an aqueous mixture of CH₃CN. The skilled artisan would readily recognize the variety of polar solvents that may be used, including without limitation water, aqueous solutions of THF, DMF, or other polar protic or polar aprotic water miscible solvents.

In another embodiment, the lactone of Formula V is formed by reacting the compound of Formula I with I₂ in a polar solvent to form a first product, and reacting the first product with NaN₃ to form a compound of Formula V.

In another embodiment, reducing is done with NaBH₄.

In another embodiment, the leaving groups are mesylate groups and the intermediate is given by one or both of the following structures:

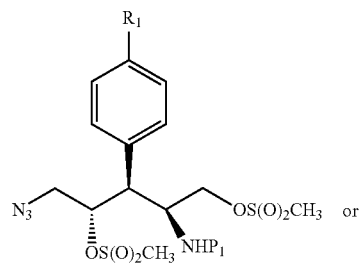
(Formula VII)

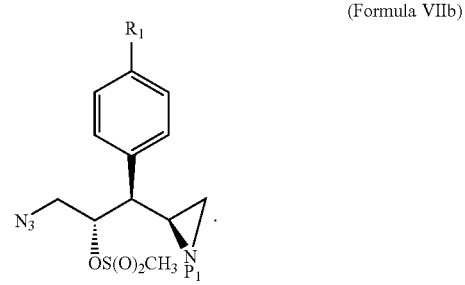
(Formula VIIb)

In another embodiment, P₁ is converted from —C(O)CF₃ into the following structure:

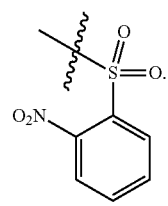 [SMILES: *S(=O)(=O)c1ccccc1[N+](=O)[O-]]

In another embodiment, R₁ is —Br, R₂ is —C(O)OCH₂CH₃ and P₁ is —S(O)C(CH₃)₃.

In another embodiment, P₁ is converted from —S(O)C(CH₃)₃ to a structure as follows:

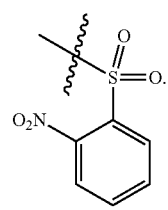 [SMILES: *S(=O)(=O)c1ccccc1[N+](=O)[O-]]

In another embodiment, the lactone of Formula V is formed by reacting the compound of Formula I with an electropositive source of halide in a polar solvent to form a first product, and reacting the first product with NaN₃ to form a compound of Formula V.

In another embodiment, the lactone of Formula V is reduced with NaBH$_4$ to form the following compound:

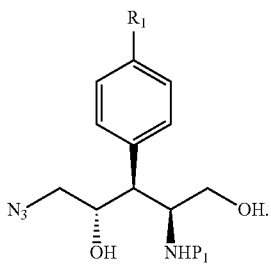

(Formula VI)

In another embodiment, the leaving groups are mesylate groups and the intermediate is given by one or both of the following structures:

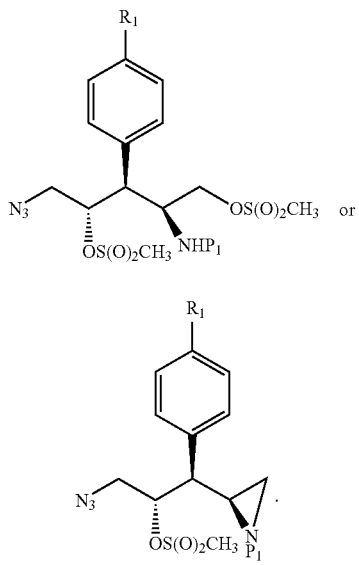

(Formula VII)

or (Formula VIIb)

Another embodiment may be directed to a method of making a compound given by the structure of Formula VIII:

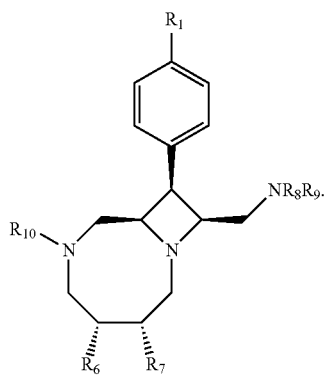

(Formula VIII)

In Formula VIII, R$_1$ is —I, —Cl, —Br, or

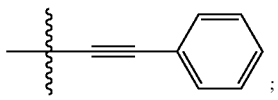

;

R$_6$ and R$_7$ are independent the same or different, and are selected from —H, alkyl, —Oalkyl, or wherein R$_6$ and R$_7$ together with the atoms to which they are attached form ring; R$_8$ and R$_9$ are independently the same or different, and are selected from —H, -alkyl, —C(O)alkyl, —S(O)$_2$alkyl, or R$_8$ and R$_9$ together with the N to which they are attached form a monocyclic ring or bicyclic ring system; R$_{10}$ is —H, straight chain or branched alkyl, —C(O)alkyl, —C(O)O-alkyl, —C(O)NH-alkyl, —C(O)aryl, —C(O)O-aryl, —C(O)NH-aryl, —C(O)heteroaryl, —C(O)O-heteroaryl, and —C(O)N-heteroaryl; wherein the alkyl, aryl and heteroaryl are optionally substituted by one or more halogens, oxygen, nitrogen, or sulfur atoms. The method includes reacting a compound given by Formula IV:

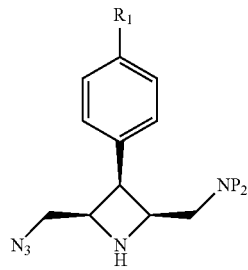

(Formula IV)

with substituted γ-hydroxyaldehyde and effecting bicyclization.

In one embodiment, the γ-hydroxyaldehyde is given by the following structure:

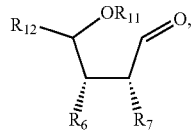

(Formula IX)

wherein R$_{11}$ is —H or an oxygen protecting group; and R$_{12}$ is —H or —CH$_2$OH.

In another embodiment, the γ-hydroxyaldehyde is

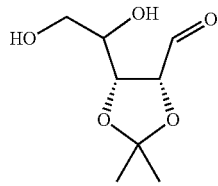

and the compound of Formula VIII is made proceeding through the following intermediate:

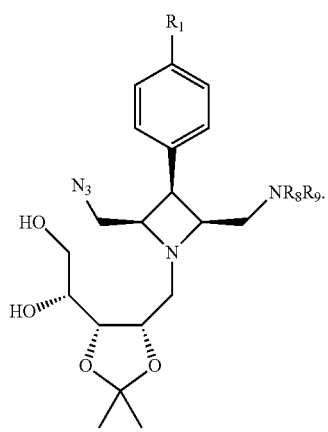

(Formula X)

In another embodiment, the method further includes oxidation and the compound of Formula VIII is made proceeding through the following intermediate:

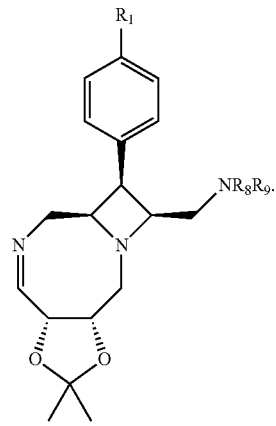

(Formula XII)

In another embodiment, the method includes further reduction and the compound of Formula VIII is made proceeding through the following intermediate:

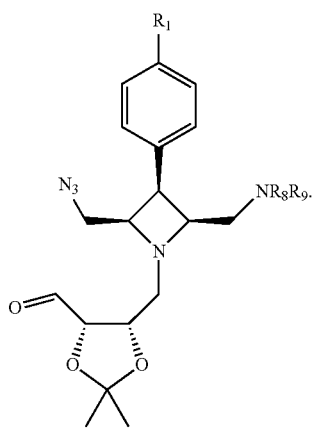

(Formula XI)

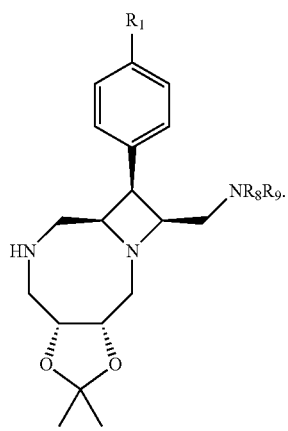

(Formula XIII)

In another embodiment, the method further includes reduction and bicyclization, and the compound of Formula VIII is made proceeding through the following intermediate:

In another embodiment, the compound of Formula XIII is reacted with 4-methoxyphenyl isocyanate and the compound of Formula VIII is given by the following structure:

(Formula XIV)

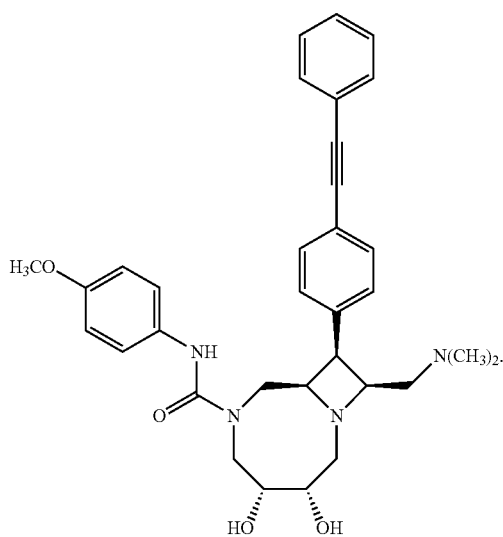

Another object of the present invention is directed to a method of forming a compound given by Formula IV (Formula IV)

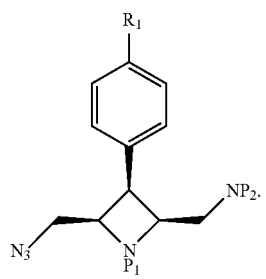

In Formula IV, $R_1$ is —I, —Cl, —Br, or

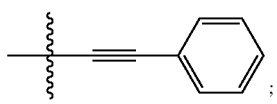

;

$P_1$ and $P_2$ are the same or different and represent nitrogen protecting groups. The method includes converting the alcoholic groups covalently attached to the unsaturated carbons of Formula VI (Formula VI)

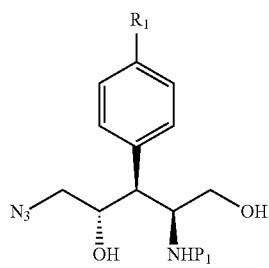

into leaving groups to form an intermediate that reacts with a nitrogen nucleophile to generate a compound of Formula IV.

In one embodiment, the leaving groups are mesylate groups and the intermediate is given by one or both of the following structures:

(Formula VIIa)

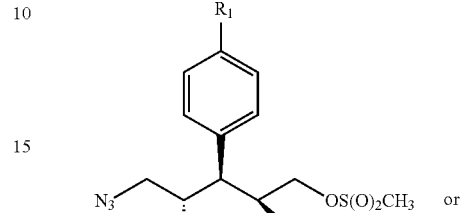

or (Formula VIIb)

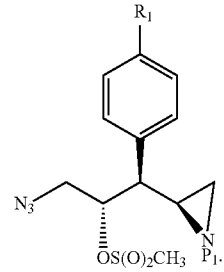

In another embodiment, the nitrogen nucleophile is phthalimide.

One beneficial discovery of the present invention is the chemoselective tandem process to prepare substituted azetidines. This may be the first or one of the first examples of a tailored nucleophilic aziridine opening in preference to an oxygen leaving group displacement and underscores the importance of ring-strain energy relief in governing chemical reactivity. Another beneficial discovery of the present invention is application of an aza-Wittig/reduction sequence to construct an eight-membered ring, directly from an azido-aldehyde.

Another embodiment is directed to a compound given by Formula I:

(Formula I)

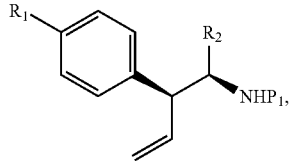

wherein in Formula I, $R_1$ is

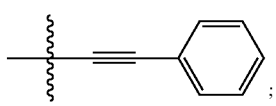

;

$R_2$ is $C(O)R_3$; $R_3$ is —O⁻ and a positive counterion is ionically associated with Formula I or $R_3$ is —OH; and $P_1$ is a nitrogen protecting group or —H.

Another embodiment is directed to a compound given by Formula IV:

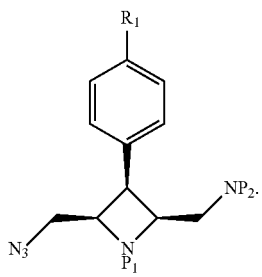
(Formula IV)

In Formula IV, $R_1$ is —I, —Cl, —Br, or

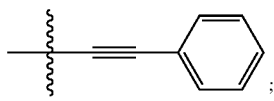
;

and $P_1$ and $P_2$ are the same or different and represent nitrogen protecting groups or —H.

Another embodiment is directed to a compound given by Formula V:

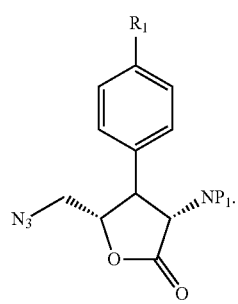
(Formula V)

In Formula V, $R_1$ is —I, —Cl, —Br, or

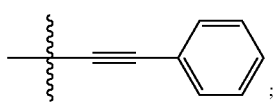
;

and $P_1$ is a nitrogen protecting group or —H.

Another embodiment is directed to a compound given by Formula VI:

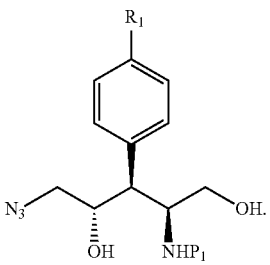
(Formula VI)

In Formula VI, $R_1$ is —I, —Cl, —Br, or

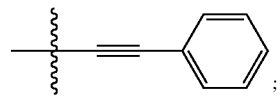
;

and $P_1$ is a nitrogen protecting group or —H.

Another embodiment is directed to a compound given by Formula VII:

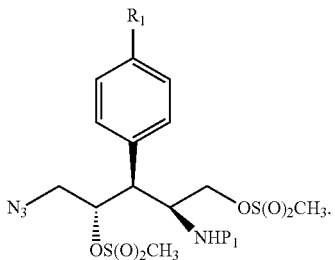
(Formula VII)

In Formula VII, $R_1$ is —I, —Cl, —Br, or

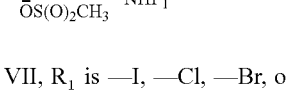
;

and $P_1$ is a nitrogen protecting group or —H.

Another embodiment is directed to a compound given by Formula VIIb:

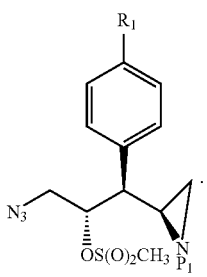
(Formula VIIb)

In Formula VIIb, $R_1$ is —I, —Cl, —Br, or

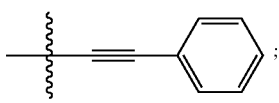 [SMILES: *C#Cc1ccccc1]

and $P_1$ is a nitrogen protecting group or —H.

Another embodiment is directed to a compound given by Formula VIII:

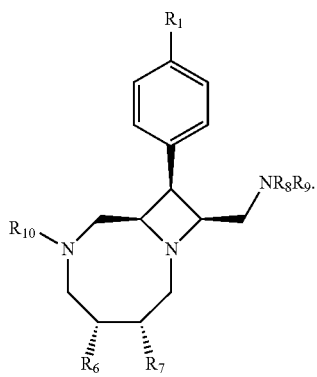
(Formula VIII)

In Formula VIII, $R_1$ is —I, —Cl, —Br, or

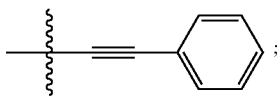 [SMILES: *C#Cc1ccccc1]

$R_6$ and $R_7$ are independently the same or different, and are selected from —H, alkyl, —Oalkyl, or wherein $R_6$ and $R_7$ together with the atoms to which they are attached form a ring; $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system; and $R_{10}$ is —H, straight chain or branched alkyl, —C(O)alkyl, —C(O)O-alkyl, —C(O)NH-alkyl, —C(O)aryl, —C(O)O-aryl, —C(O)NH-aryl, —C(O)heteroaryl, —C(O)O-heteroaryl, and —C(O)N-heteroaryl, wherein the alkyl, aryl and heteroaryl are substituted by one or more hydrogen, halogen, oxygen, nitrogen, or sulfur atoms.

Another embodiment is directed to a compound given by Formula X:

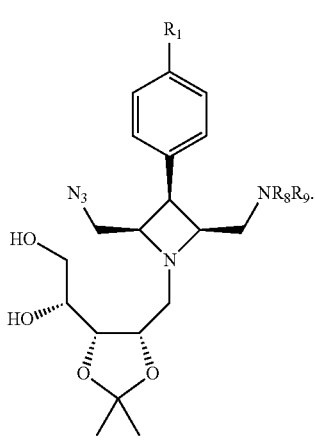
(Formula X)

In Formula X, $R_1$ is —I, —Cl, —Br, or

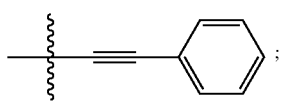 [SMILES: *C#Cc1ccccc1]

and $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more hydrogen, halogen, oxygen, nitrogen, or sulfur atoms.

Another embodiment is directed to a compound given by Formula XI:

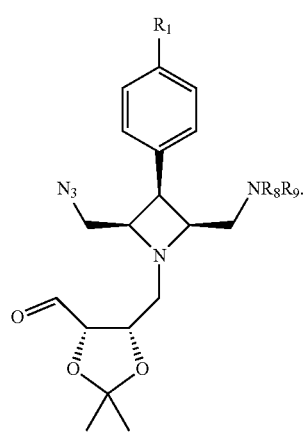
(Formula XI)

In Formula XI, $R_1$ is —I, —Cl, —Br, or

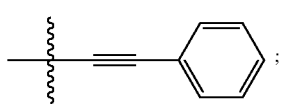 [SMILES: *C#Cc1ccccc1]

and $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more hydrogen, halogen, oxygen, nitrogen, or sulfur atoms.

Another embodiment is directed to a compound given by Formula XII:

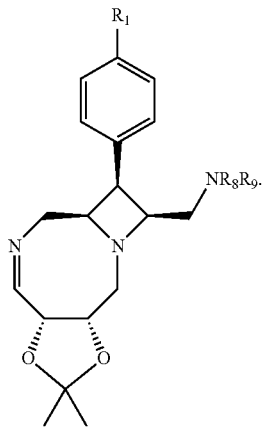

(Formula XII)

In Formula XII, $R_1$ is —I, —Cl, —Br, or

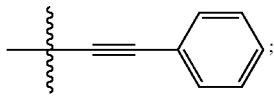

and $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more halogen, hydrogen, oxygen, nitrogen, or sulfur atoms.

Another embodiment is directed to a compound given by Formula XIII:

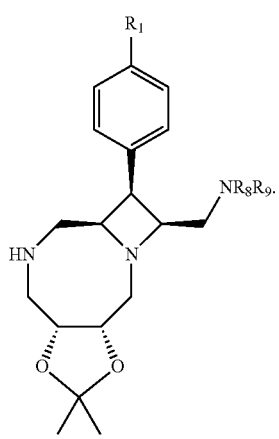

(Formula XIII)

In Formula XIII, $R_1$ is —I, —Cl, —Br, or

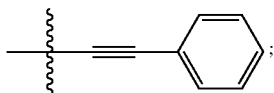

and $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more halogen, hydrogen, oxygen, nitrogen, or sulfur atoms.

Another embodiment is directed to a compound given by Formula XV:

(Formula XV)

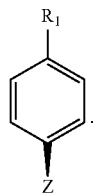

In Formula XV, $R_1$ is —I, —Cl, —Br, or

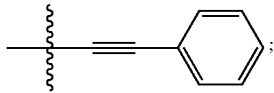

and

Z is a 4-membered nitrogen-containing heterocycle selected from one of the following:

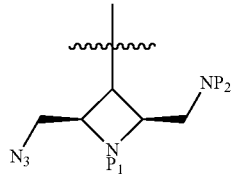

$P_1$ and $P_2$ are the same or different and are nitrogen protecting groups or —H;

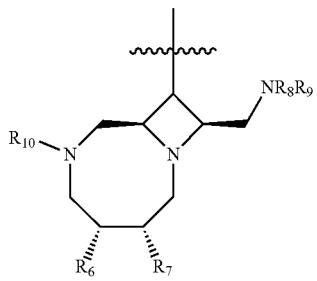

$R_6$ and $R_7$ are independently the same or different, and are selected from —H, alkyl, —Oalkyl, or wherein $R_6$ and $R_7$ together with the atoms to which they are attached form a ring; $R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system; and $R_{10}$ is —H, straight chain or branched alkyl, —C(O)alkyl, —C(O)O-alkyl, —C(O)NH-alkyl, —C(O)aryl, —C(O)O-aryl, —C(O)NH-aryl, —C(O)heteroaryl, —C(O)O-heteroaryl, and —C(O)N-heteroaryl, wherein the alkyl, aryl and heteroaryl are substituted by one or more halogen, hydrogen, oxygen, nitrogen, or sulfur atoms;

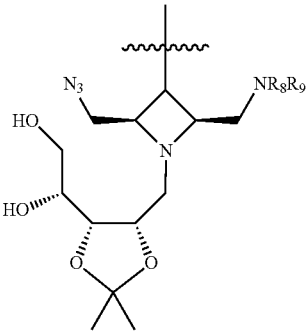

$R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more halogen, hydrogen, oxygen, nitrogen, or sulfur atoms;

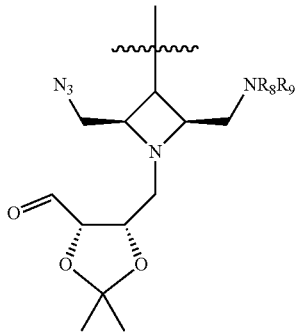

$R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more halogen, hydrogen oxygen, nitrogen, or sulfur atoms;

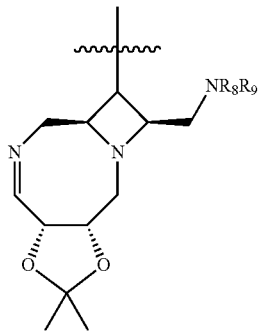

$R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is substituted by one or more halogen, hydrogen oxygen, nitrogen, or sulfur atoms; and

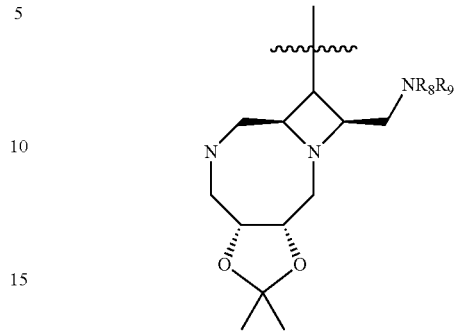

$R_8$ and $R_9$ are independently the same or different, and are selected from —H, -alkyl, —C(O)alkyl, —S(O)$_2$alkyl, or $R_8$ and $R_9$ together with the N to which they are attached form a monocyclic ring or bicyclic ring system, wherein the alkyl is optionally substituted by one or more halogen, hydrogen, oxygen, nitrogen, or sulfur atoms.

Another embodiment is directed to a compound given by Formula XV:

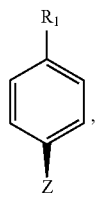

(Formula XV)

wherein $R_1$ is —I, —Cl, —Br, or

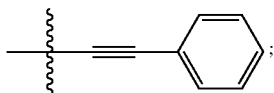

wherein in Formula XV, Z is selected from one of the following:

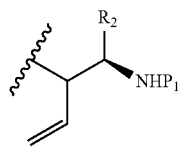

$R_2$ is $C(O)R_3$; $R_3$ is —O⁻ and a positive counterion is ionically associated with Formula XVI, or $R_3$ is —OH; and $P_1$ is a nitrogen protecting group or —H;

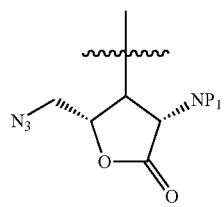

$P_1$ is a nitrogen protecting group or —H;

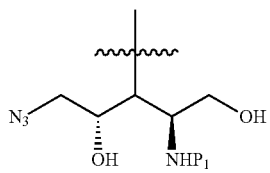

$P_1$ is a nitrogen protecting group or —H;

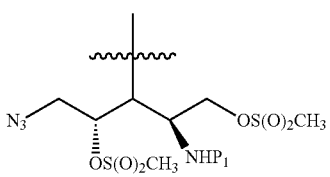

$P_1$ is a nitrogen protecting group or —H; and

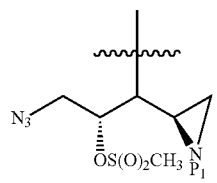

$P_1$ is a nitrogen protecting group or —H;
Or a pharmaceutically acceptable salt thereof Compounds provided herein, including but not limited to compounds of Formulas I, IV, V, VI, VII, VIIb, VIII, X, XI, XII, XIII, and XV may be provided as pharmaceutically acceptable salts. "Pharmaceutically acceptable salt" as used herein refer to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

Other aspects and advantages of the invention will be apparent from the following description, drawings and the appended claims.

DETAILED DESCRIPTION OF THE INVENTION

Figure 1:
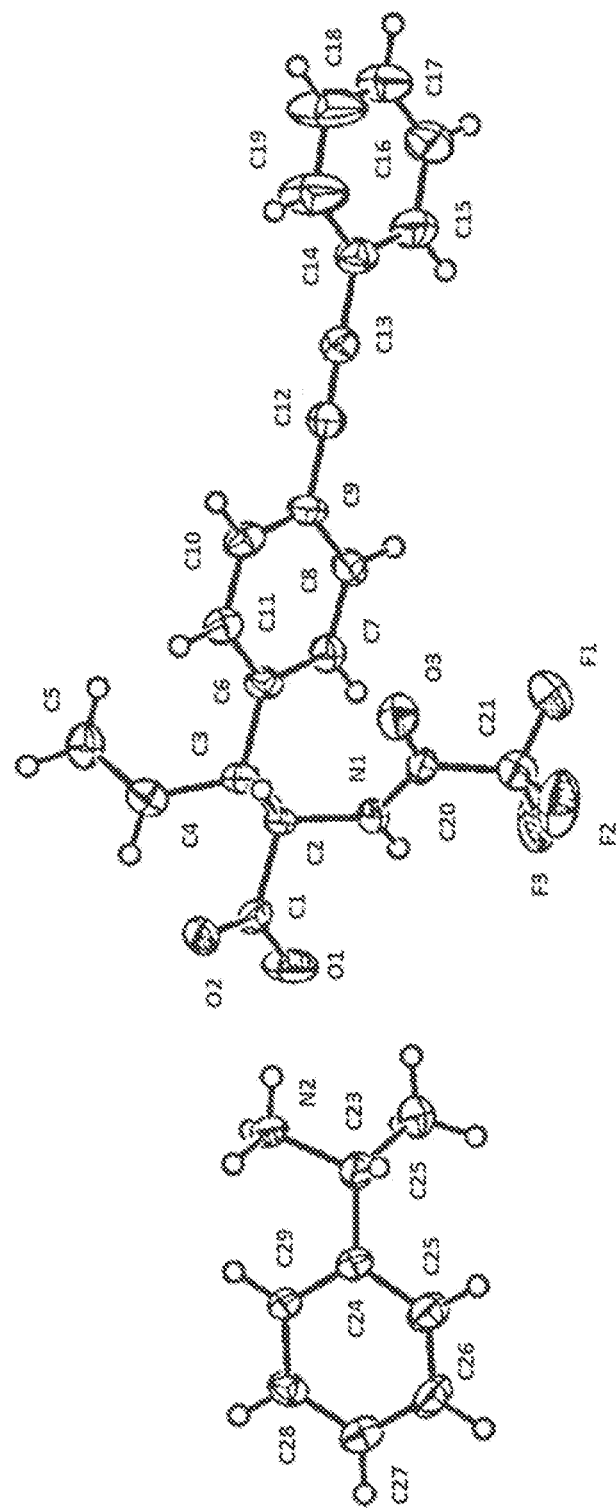
FIG. 1 shows an ORTEP projection for Compound 5.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are described herein.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

The term "alkyl" includes branched, straight chain and cyclic, substituted or unsubstituted saturated aliphatic hydrocarbon groups. Alkyl groups can comprise about 1 to about 24 carbon atoms ("C1-C24"), about 7 to about 24 carbon atoms ("C7-C24"), about 8 to about 24 carbon atoms ("C8-C24"), or about 9 to about 24 carbon atoms ("C9-C24"). Alkyl groups can also comprise about 1 to about 8 carbon atoms ("C1-C8"), about 1 to about 6 carbon atoms ("C1-C6"), or about 1 to about 3 carbon atoms ("C1-C3"). Examples of C1-C6 alkyl groups include, but are not limited to, methyl, ethyl, propyl, isopropyl, butyl, sec-butyl, tert-butyl, pentyl, isopentyl, neopentyl, hexyl, isohexyl, cyclohexyl, cyclohexylmethyl, cyclopropylmethyl and neohexyl radicals.

The term "aryl" includes a 6- to 14-membered monocyclic, bicyclic or tricyclic aromatic hydrocarbon ring system. Examples of an aryl group include phenyl and naphthyl.

The term "heteroaryl" includes an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl.

Oxygen protecting groups include, without limitation for example, benzyl or substituted benzyl, silyl or substituted silyl groups, acetyl or other ester protection groups, methoxy methyl or other methoxy ethers. The skilled artisan would recognize other acceptable protecting groups such as those identified in *Greene's Protective Groups in Organic Synthesis*, Fifth ed., Peter G. M. Wuts, John Wiley & Sons, Inc. (2014), fully incorporated by reference herein.

The skilled artisan would recognize a wide variety of nitrogen protecting groups that may be used according to embodiments of the invention. See also *Greene's Protective Groups in Organic Synthesis*, Fifth ed., which is fully incorporated by reference herein. Useful nitrogen protecting groups may include, for example, but are not limited to 9-fluorenylmethyl carbamate; t-butyl carbamate; 2-nitrobenzenesulfonyl; 4-nitrobenzenesulfonyl; benzyl carbamate; acetamide; trifluoroacetamide; phthalimide; benzylamine; triphenylmethylamine; benzylideneamine; and p-toluenesulfonamide.

Abbreviations. XPhos-Pd-G3 (XPhos G3) is (2-Dicyclohexylphosphino-2',4',6'-triisopropyl-1,1'-biphenyl)[2-(2'-amino-1,1'-biphenyl)]palladium(II) methanesulfonate, XPhos-G3-Palladacycle (Sigma-Aldrich). Dess Martin periodinane is 1,1,1-Tris(acetyloxy)-1,1-dihydro-1,2-benziodoxol-3-(1H)-one (Sigma-Aldrich). MTBE is methyl tertiary-butyl ether. As used herein, "Ns" or "nosyl" refers to a 2-nitrophenylsulfonyl group; "Ms" or "mesyl" refers to a methanesulfonyl group; and "TFA" refers to a trifluoracetyl group.

While only certain stereoisomers may be represented in any given claim, the skilled artisan would appreciate that the enantiomer or other stereoisomers could be made through manufacture of the appropriate corresponding chiral starting material or intermediate.

If there is a discrepancy between a depicted structure and a name given that structure, the depicted structure controls. In addition, if the stereochemistry of a structure or a portion of a structure is not indicated with, for example, bold or dashed lines, the structure or portion of the structure is to be interpreted as encompassing all stereoisomers of it.

Route A Synthesis

Esterification of 4-bromocinnamoic Acid to Give (methyl (E)-3-(4-bromophenyl)acrylate) 1

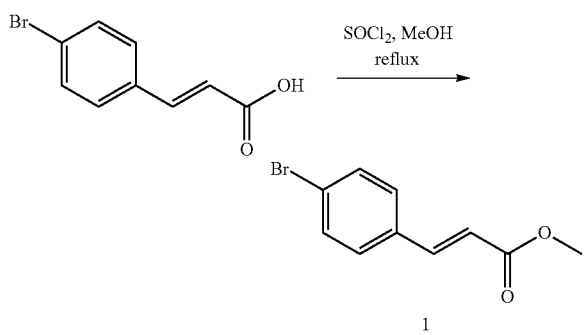

Thionyl chloride (176 mL, 2422 mmol) was added dropwise to a white suspension of 4-bromocinnamoic acid (500 g, 2202 mmol) in methanol (3000 mL) over 20 min during which the reaction temperature remained below 40° C. The mixture was then heated to reflux for 1 h, during which it became homogeneous. The solution was slowly allowed to room temperature to give a white suspension. It was filtered and the filter cake washed two times with cold methanol to give 1 as white solid. The filtrate was concentrated to half of the original volume and was again filtered and the filter cake washed with cold methanol. The procedure was repeated two more times to give additional 1 (523 g combined, 98% yield).

$^1$H NMR (400 MHz, CDCl$_3$) δ 7.62 (d, J=16.0 Hz, 1H), 7.52 (d, J=8.2 Hz, 2H), 7.38 (d, J=8.6 Hz, 2H), 6.43 (d, J=16.0 Hz, 1H), 3.81 (s, 3H); $^{13}$C NMR (75 MHz, CDCl$_3$) δ 167.1, 143.4, 133.2, 132.1, 129.4, 124.5, 118.5, 51.8.

Sonogashira Reaction of 1 to Give (methyl (E)-3-(4-(phenylethynyl)phenyl)acrylate) 2

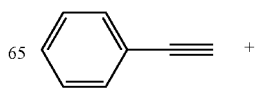

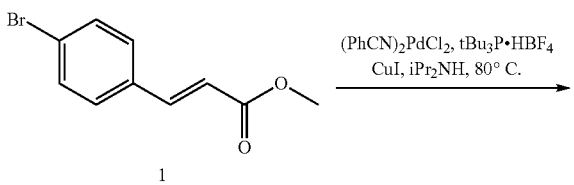
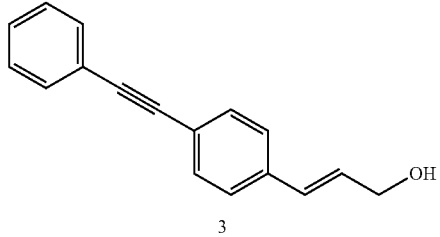

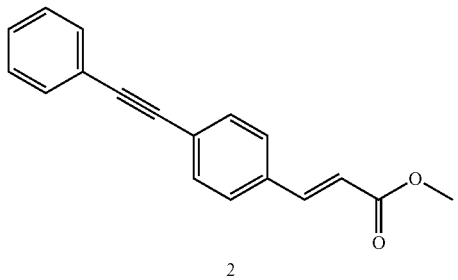

1 (285 g, 1180 mmol) was dissolved in diisopropylamine (2500 ml) to give a clear, homogeneous solution. It was sparged with nitrogen gas for 30 min before copper(I) iodide (0.169 g, 0.885 mmol), bis(benzonitrile)palladium(II) chloride (0.453 g, 1.18 mmol), and tri-tert-butylphosphonium tetrafluoroborate (0.685 g, 2.36 mmol) were added. The mixture was heated to 80° C. before phenylacetylene (136 mL, 1239 mmol) was added in portions to firstly initiate the reaction, as indicated by increase of the internal temperature till reflux and formation of precipitate, and then maintain reflux of the exothermic reaction. After the addition had been complete, the mixture was stirred at 80° C. for an additional hour, and then slowly allowed to 50° C. when the reaction was quenched with water (2000 mL). The mixture was allowed to room temperature with stirring and then filtered. The filter cake was washed with water (200 mL×3), and then dried under vacuum at 40° C. to give 2 (296 g, 96%) as white solid, which is pure based on NMR spectra.

$^1$H NMR (400 MHz, CDCl$_3$) δ 7.69 (d, J=16.0 Hz, 1H), 7.56-7.50 (m, 6H), 7.38-7.35 (m, 3H), 6.46 (d, J=16.0 Hz, 1H), 3.83 (s, 3H); $^{13}$C NMR (75 MHz, CDCl$_3$) δ 167.2, 143.9, 134.1, 132.0, 131.6, 128.5, 128.4, 128.0, 125.2, 122.9, 118.4, 91.6, 89.0, 51.7.

Reduction of 2 to Give ((E)-3-(4-(phenylethynyl)phenyl)prop-2-en-1-ol) 3

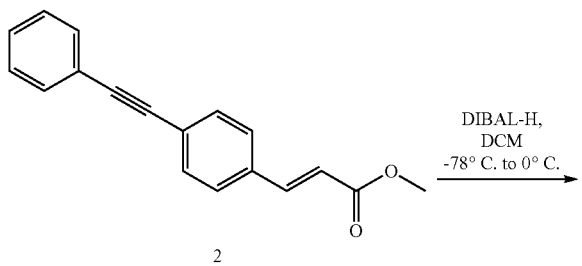

A clear, colorless solution of 2 (210 g, 801 mmol) in dichloromethane (3150 mmol) was cooled in a dry ice-acetone bath to −78° C., during which the solution turned into a white suspension. A solution of diisobutylaluminum hydride (25 wt. % in toluene, 934 g, 1641 mmol) was slowly added and then the mixture slowly allowed to −20° C. over 12 h. The reaction was carefully quenched with a solution of potassium sodium tartrate tetrahydrate (926 g, 3282 mmol) in water (4200 mL) and the mixture was stirred at room temperature for 12 h. The two phases were separated and the aqueous phase was extracted with dichloromethane (1700 mL×4). The combined organic phases were dried over anhydrous sodium sulfate and concentrated to give 3 (184 g, 98%) as white solid, which is pure based on NMR spectra.

$^1$H NMR (400 MHz, CDCl$_3$) δ 7.55-7.48 (m, 4H), 7.39-7.34 (m, 5H), 6.63 (d, J=16.1 Hz, 1H), 6.41 (dt, J=16.0, 5.4 Hz, 1H), 4.36 (dd, J=5.5, 1.6 Hz, 2H); $^{13}$C NMR (75 MHz, CDCl$_3$) δ 136.6, 131.8, 131.6, 130.4, 129.5, 128.3, 128.3, 126.4, 123.2, 122.4, 90.1, 89.4, 63.6.

Esterification of 3 with N-(trifluoroacetyl)glycine to Give ((E)-3-(4-(phenylethynyl)phenyl)allyl (2,2,2-trifluoroacetyl)glycinate) 4

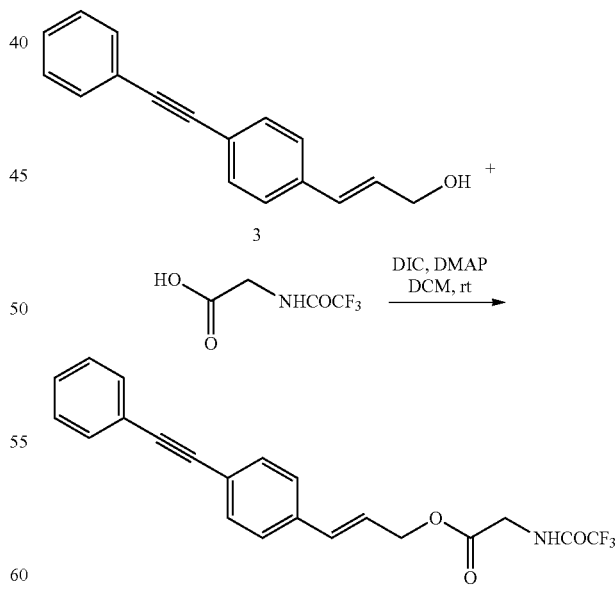

A mixture of 3 (184 g, 785 mmol), N-(trifluoroacetyl)glycine (136 g, 793 mmol) and 4-(dimethylamino)pyridine (9.59 g, 78.5 mmol) was taken into dichloromethane (1840 mL) to give a yellow suspension. It was cooled in an ice bath till 10° C. when N,N'-diisopropylcarbodiimide (128 mL, 825 mmol) was added in portions while the internal temperature was maintained below 15° C. The mixture was slowly allowed to room temperature and stirred overnight. The mixture was filtered and the filter cake was washed with methylene chloride (50 mL×3). The filtrate was taken into a mixed solvent of ethyl acetate/methyl tert-butyl ether (1:1, 3680 mL), washed with aqueous sodium bicarbonate (400 mL×2) and brine (400 mL). The organic phase was dried over anhydrous sodium sulfate and concentrated. The residue was crystalized in isopropanol to give 4 (240 g, 79%) as white solid.

$^1$H NMR (400 MHz, CDCl$_3$) δ 7.56-7.50 (m, 4H), 7.40-7.34 (m, 5H), 6.90 (br s, 1H), 6. 6.69 (d, J=15.6 Hz, 1H), 6.31 (dt, J=16.0, 6.6 Hz, 1H), 4.88 (dd, J=6.6, 1.1 Hz, 2H), 4.19 (d, J=5.0 Hz, 1H); $^{13}$C NMR (75 MHz, CDCl$_3$) δ 168.0, 135.5, 134.9, 131.9, 131.6, 128.4, 126.6, 123.3, 123.1, 122.5, 90.5, 89.1, 66.6, 41.4.

Claisen Rearrangement of 4 and Chiral Resolution Using (R)-(+)-1-phenylethylamine to Give ((R)-1-phenylethan-1-aminium (2S,3S)-3-(4-(phenylethynyl)phenyl)-2-(2,2,2-trifluoroacetamido)pent-4-enoate) 5

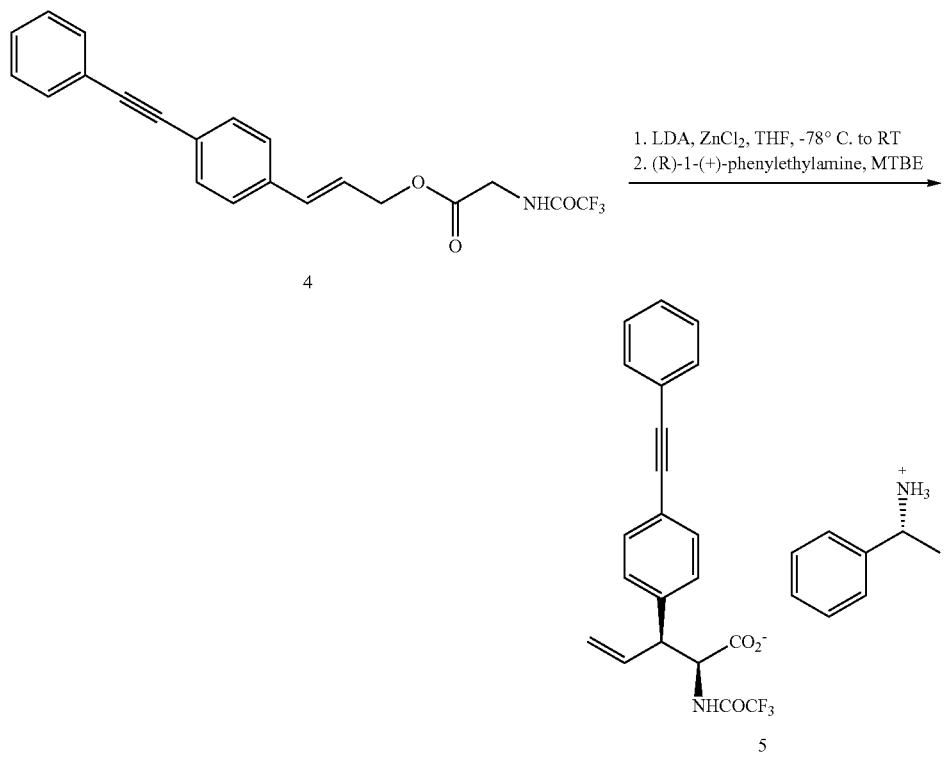

Preparation of lithium diisopropylamide (LDA): A solution of diisopropylamine (22.8 mL, 160 mmol) in tetrahydrofuran (130 mL) was cooled in an ice bath and treated with a solution of n-butyllithium (2.5 M in hexanes, 62.0 mL, 155 mmol) slowly while maintaining the internal temperature below 20° C. The ice bath was removed and the mixture was stirred at room temperature for 30 min.

In a separate vessel, a solution of 4 (20.0 g, 51.6 mmol) in tetrahydrofuran (140 mL) was cooled in a dry ice-acetone bath to give a yellow suspension. It was treated with a solution of zinc chloride (1.9 M in 2-methyltetrahydrofuran, 40.8 mL, 77.4 mmol) while maintaining the internal temperature below −60 degree. To this mixture was slowly added the LDA solution while maintaining the internal temperature below −65° C., during which the mixture turned into a dark blue homogeneous solution toward the end of the addition. The reaction mixture was maintained at the temperature for 60 min. The cooling bath was removed and the reaction mixture slowly allowed to room temperature during which it turned dark orange. The reaction was quenched with hydrochloric acid (1 M, 336 mL, 336 mmol) during which the internal temperature rise to 35° C. The two phases were separated and the aqueous phase was extracted with methyl tert-butyl ether (160 mL×2). The combined organic phases were concentrated and the residue taken into methyl tert-butyl ether (160 mL). The mixture was heated to reflux temperature to give a mostly clear solution. It was treated with (R)-(+)-1-phenylethylamine (12.5 g, 103 mmol) to give a clear solution from which precipitate soon started to form. With agitation, the mixture was slowly allowed to room temperature, and then cooled in an ice bath. The product was filtered, washed with methyl tert-butyl ether (20 mL×2) and dried under vacuum to give 5 (10.7 g, 40.8% yield, e.r.=16.8:1) as white solid.

$^1$H NMR (400 MHz, MeOH-d$_4$) δ 7.52-7.49 (m, 2H), 7.46-7.39 (m, 7H), 7.39-7.34 (m, 3H), 7.28 (d, J=8.2 Hz, 2H), 6.24-6.14 (m, 1H), 5.13-5.09 (m, 2H), 4.70 (d, 8.2 Hz, 1H), 4.44 (q, J=7.0 Hz, 1H), 3.86 (t, J=8.2 Hz, 1H), 1.63 (d, J=7.0 Hz, 3H); $^{13}$C NMR (75 MHz, MeOH-d$_4$) δ 175.5, 142.2, 140.1, 139.1, 132.7, 132.6, 130.5, 130.3, 130.0, 129.7, 129.5, 127.7, 124.9, 123.2, 117.4, 90.2, 90.1, 61.0, 54.3, 52.5, 21.0.

Iodolactonization of 5 and Substitution with Sodium Azide to Give (N-((3S,4S,5S)-5-(azidomethyl)-2-oxo-4-(4-(phenylethynyl)phenyl)tetrahydrofuran-3-yl)-2,2,2-trifluoroacetamide) 7

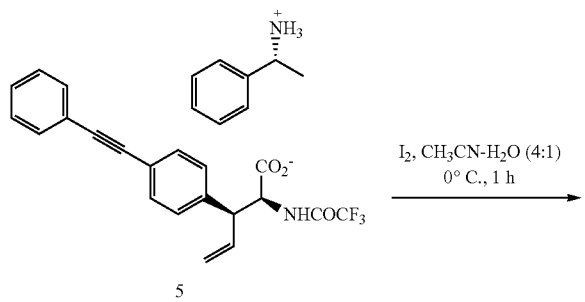

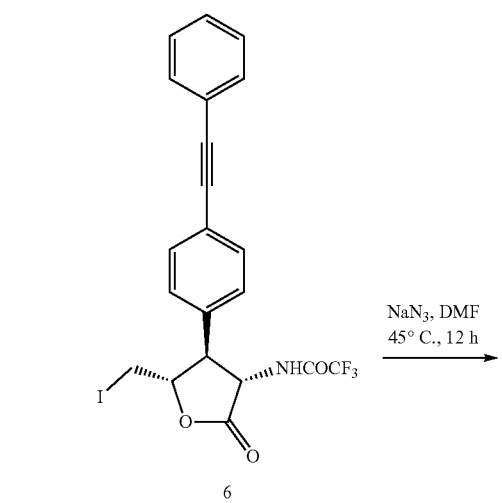

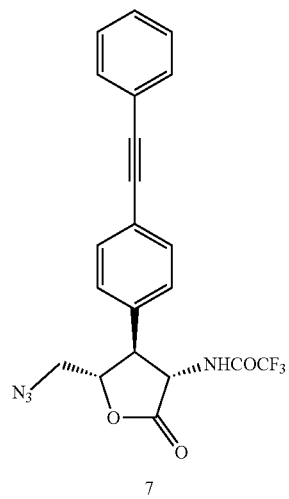

A white, milky suspension of 5 (30.9 g, 60.8 mmol) in acetonitrile (494 mL) and water 124 mL) was cooled to 0° C. and treated with iodine (30.8 g) to give a dark red solution, which was stirred at the temperature for 1 h. The reaction was quenched by treating the mixture with sodium thiosulfate (28.8 g, 182 mmol) and stirring for 10 min during which it turned light yellow. The mixture was taken into methyl tert-butyl ether (500 mL) and the two phases were separated. The organic phase was washed with 1 M hydrochloric acid (150 mL) and brine (150 mL). The aqueous phase was back extracted with methyl tert-butyl ether. The combined organic phases were dried over anhydrous sodium sulfate and concentrated to give crude (2,2,2-trifluoro-N-((3S,4S,5S)-5-(iodomethyl)-2-oxo-4-(4-(phenylethynyl)phenyl)tetrahydrofuran-3-yl)acetamide) 6 as a red gum.

The above crude 6 was taken into N,N-dimethylformamide (185 mL) and treated with sodium azide (15.8 g, 243 mmol). The mixture was stirred at room temperature for 12 h, then heated to 45° C. and stirred for an additional 12 h. The mixture was taken into methyl tert-butyl ether (400 mL), washed with water (300 mL) and brine (300 mL). The aqueous phase was back extracted with methyl tert-butyl ether (300 mL×2). The combined organic phases were dried over anhydrous sodium sulfate and concentrated. The crude was passed through a short pad of silica gel (130 g) eluting with 50% ethyl acetate in heptane (100 mL). The filtrate was concentrated to give 7 as light yellow foamy solid, which was used without purification.

Preparation of Amino Diol 9 from Azidolactone ((2S,3S,4S)-2-amino-5-azido-3-(4-(phenylethynyl)phenyl)pentane-1,4-diol) 7

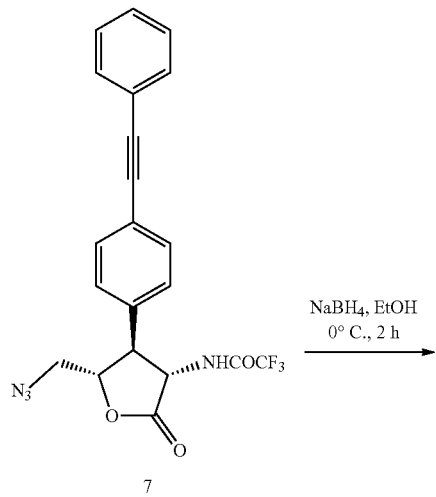

7

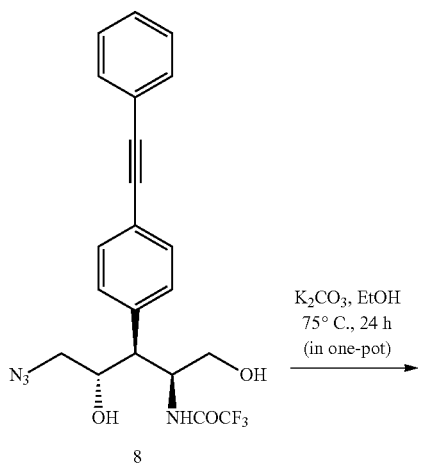

8

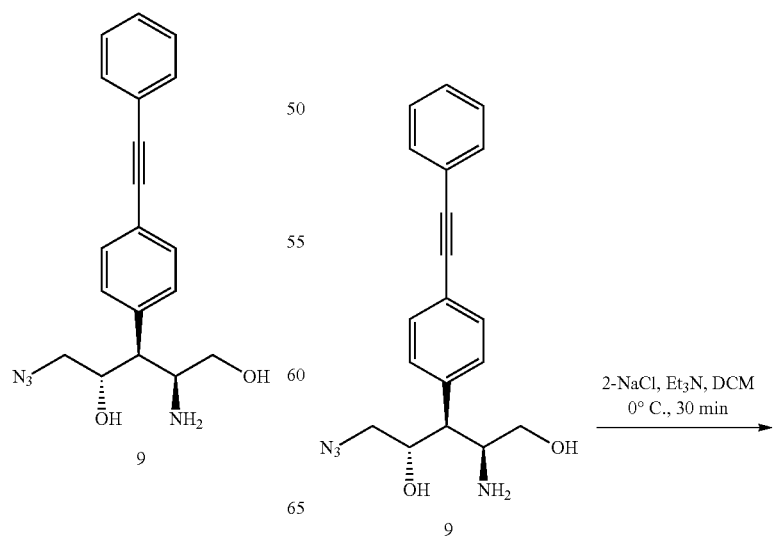

9

The above crude 7 (26.0 g, 60.8 mmol) was taken into ethanol (260 mL) to give a colorless solution. It was cooled in an ice bath and treated with sodium borohydride (2.76 g, 73.0 mmol). The mixture was stirred at the temperature for 2 h to give a white suspension. The ice bath was removed and then mixture was allowed to rt, and it was then brought to 45° C. until bubbles cease to form and the mixture became homogeneous. The solution was treated with potassium carbonate (25.2 g, 182 mmol) and water (13 mL), and stirred at the temperature for 24 h. The mixture was concentrated and the residue was taken into methylene chloride (390 mL). It was treated with celite (26 g) and filtered through a pad of celite, rinsing with methylene chloride (260 mL×2). The filtrate was concentrated to give an orange solid, which was filtered through a pad of silica gel (160 g) eluting with 20% methanol in dichloromethane (conditioned with 1% aqueous ammonia, 2000 mL). The filtrate was concentrated and the residue crystallized (in isopropyl acetate/isopropanol=3:1, mother liquor concentrated and further crystallized acetonitrile, then ethyl acetate) to give 9 as white solid (7.01 g). Another fraction of 9 was obtained as crude in the mother liquor (7.84 g, based on 9.8 g of concentrate with 80% purity as shown by ELSD, 73% combined yield from 5).

$^1$H NMR (400 MHz, MeOH-$d_4$) δ 7.53-7.49 (m, 4H), 7.40-7.36 (m, 3H), 7.30 (d, J=8.2 Hz, 2H), 4.31 (ddd, J=9.8, 6.2, 2.7 Hz, 1H), 3.49-3.45 (m, 1H), 3.40 (dd, J=10.6, 6.3 Hz, 1H), 3.33-3.32 (m, 1H), 3.29 (dd, J=10.5, 7.4 Hz, 1H), 3.15 (dd, J=12.7, 3.0 Hz, 1H), 3.03 (dd, J=12.5, 6.6 Hz, 1H), 3.00 (dd, J=9.7, 3.5 Hz, 1H); $^{13}$C NMR (75 MHz, MeOH-$d_4$) δ 138.4, 131.2, 131.1, 129.4, 128.1, 128.0, 123.1, 122.0, 88.9, 88.4, 70.8, 64.4, 55.6, 52.4, 50.1.

One-Pot N-Nosylation and Bis-O-Mesylation of 9; Tandem N-Nucleophilic Substitutions to Give Azetidine (2-(((2S,3S,4R)-4-(azidomethyl)-1-((2-nitrophenyl)sulfonyl)-3-(4-(phenylethynyl)phenyl)azetidin-2-yl)methyl)isoindoline-1,3-dione) 12

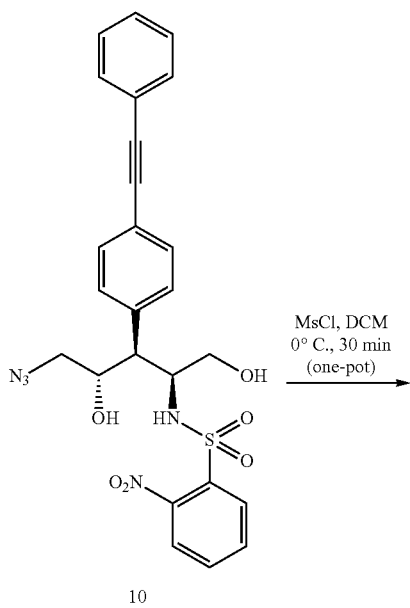

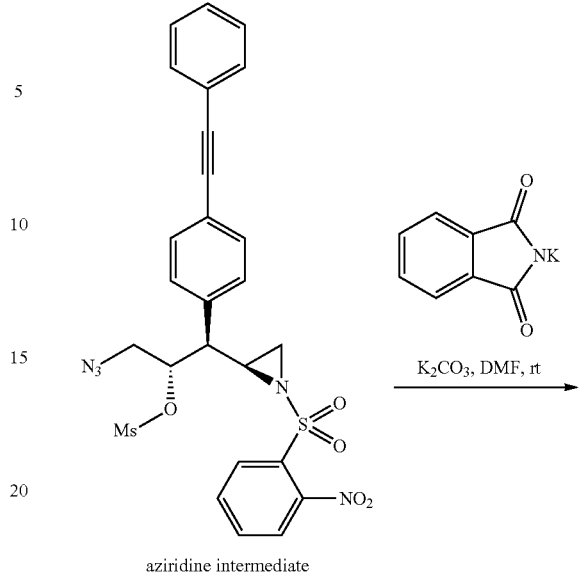

aziridine intermediate

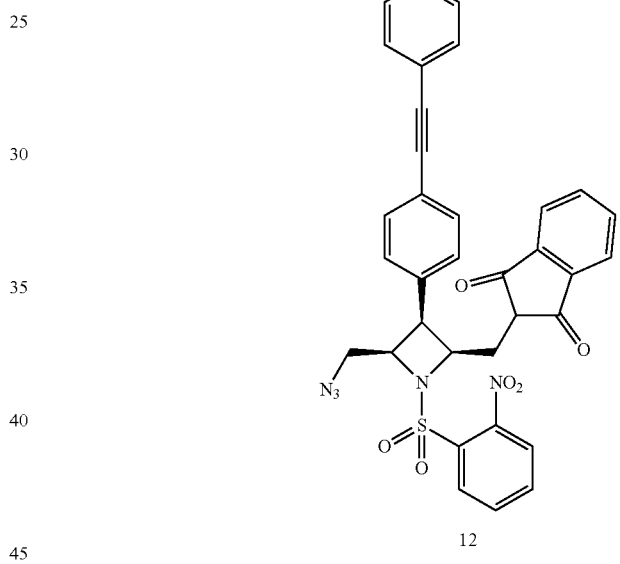

12

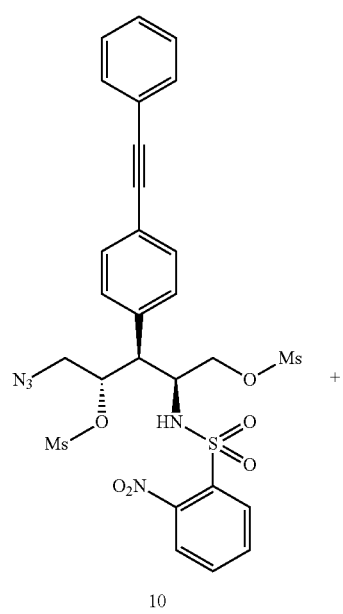

A suspension of 9 (2.00 g, 5.95 mmol) and triethylamine (4.97 mL, 35.7 mmol) in dichloromethane (20 mL) was cooled in an ice bath, and treated with a solution of 2-nitrobenzenesulfonyl chloride (1.98 g, 8.92 mmol) in dichloromethane (10 mL) while maintaining an internal temperature below 6° C. The mixture was stirred at the temperature for 30 min during which it turned homogeneous. The solution was then treated with methanesulfonyl chloride (1.39 mL, 17.8 mmol) and stirred at the temperature for 30 min. The reaction was quenched with aqueous sodium hydroxide (1 M, 100 mL) and the mixture was taken into ethyl acetate (300 mL). The organic phase was separated, washed with brine (50 mL), and concentrated to give a crude consisting of bis-mesylate 11 and the aziridine intermediate.

The above crude was taken into N,N-dimethylformamide (20 mL), treated with potassium carbonate (2.47 g, 17.8 mmol), potassium phthalimide (1.65 g, 8.92 mmol), and stirred at room temperature for 60 h. The reaction mixture was taken into ethyl acetate (400 mL), washed with water (100 mL), brine (100 mL), and concentrated. The residue was taken into isopropanol (30 mL) and boiled to give a homogeneous solution, which was slowly allowed to room temperature, with agitation, during which the product precipitated. The product was filtered, washed with isopropanol (10 mL×2), and dried under vacuum to give 12 (3.14 g, 83% yield) as off-white solid.

$^1$H NMR (400 MHz, CDCl$_3$) δ 8.15 (dd, J=7.8, 1.5 Hz, 1H), 7.85-7.75 (m, 4H), 7.72-7.69 (m, 3H), 7.61 (d, J=8.6 Hz, 2H), 7.57-7.54 (m, 2H), 7.45 (d, J=8.2 Hz, 2H), 7.39-7.35 (m, 3H), 4.93 (dt, J=8.2, 6.7 Hz, 1H), 4.55 (dt, J=9.3, 3.9 Hz, 1H), 4.23 (dd, J=14.4, 6.2 Hz, 1H), 3.79 (t, J=8.6 Hz, 1H), 3.75 (dd, J=14.4, 6.6 Hz, 1H), 3.71 (dd, J=12.9, 5.1 Hz, 1H), 3.60 (dd, J=12.8, 9.3 Hz, 1H); $^{13}$C NMR (75 MHz, CDCl$_3$) δ 167.6, 149.3, 134.8, 134.0, 132.6, 132.2, 132.0, 131.8, 131.7, 131.6, 130.5, 128.4, 128.3, 127.4, 124.3, 123.5, 123.3, 123.1, 90.4, 88.8, 62.5, 61.9, 48.7, 42.4, 37.5.

Preparation of (2-(((2S,3S,4R)-4-(azidomethyl)-1-(((4S,5R)-5-((R)-1,2-dihydroxyethyl)-2,2-dimethyl-1,3-dioxolan-4-yl)methyl)-3-(4-(phenylethynyl)phenyl)azetidin-2-yl)methyl)isoindoline-1,3-dione) 15 by Deprotection and Reductive Amination of 12

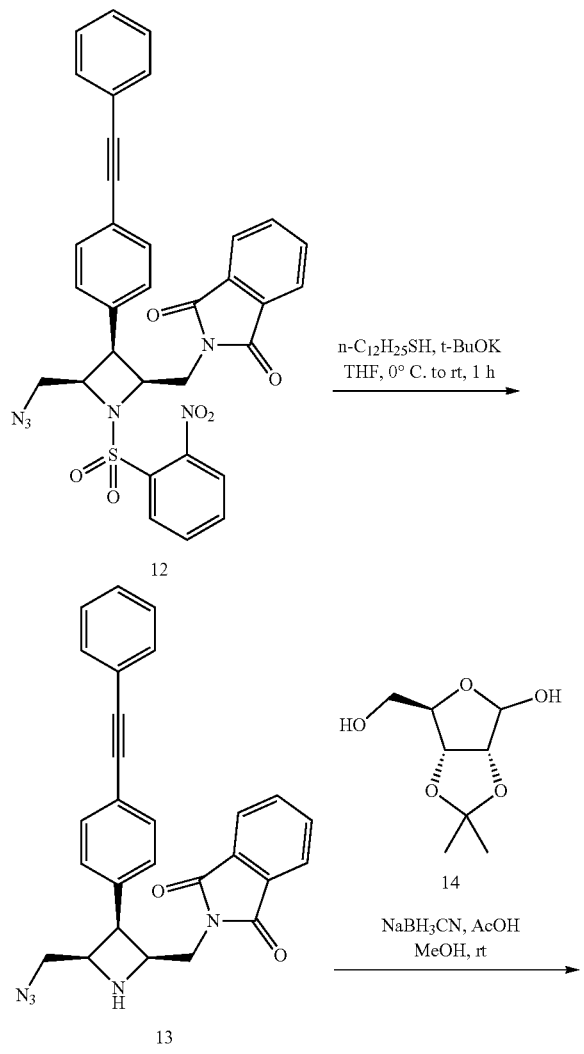

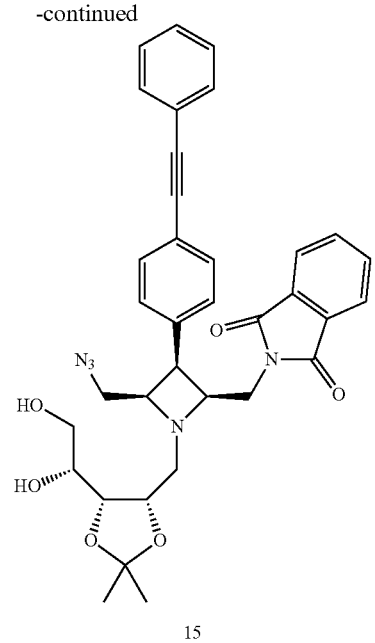

A clear, colorless solution of 12 (5.84 g, 9.23 mmol) and 1-dodecanethiol (2.65 mL, 11.1 mmol) in tetrahydrofuran (70 mL) was cooled in an ice bath to an internal temperature of 4° C. A solution of potassium tert-butoxide (1 M in THF, 11.1 mL, 11.1 mmol) was added dropwise while maintaining the internal temperature below 10° C., during which the mixture turned dark red. The ice bath was removed and the mixture was allowed to room temperature. The mixture was stirred at the temperature for 1 h, then quenched with aqueous sodium bicarbonate (100 mL) and was taken into ethyl acetate (200 mL). The two phases were separated and the aqueous phase was extracted with ethyl acetate (150 mL×3). The combined organic phases were dried over anhydrous sodium sulfate and then concentrated to give crude 13 as yellow gum.

The crude 13 was combined with 14 (2.11 g, 11.1 mmol) and taken into methanol (70 mL) to give a yellow solution, which was treated with acetic acid (2.64 mL, 46.2 mmol) and sodium cyanoborohydride (0.696 g, 11.1 mmol). The solution was stirred at room temperature for 24 h before treating with additional acetic acid (2.64 mL, 46.2 mmol) and sodium cyanoborohydride (0.300 g, 4.78 mmol). After 12 h, the third portion of sodium cyanoborohydride (0.300 g, 4.78 mmol) was added and the mixture was stirred for an additional 6 h. The reaction mixture was taken into ethyl acetate (200 mL) and washed with 1 M sodium hydroxide (100 mL). The aqueous phase was separated and back extracted with ethyl acetate (200 mL). The combined organic phases were washed with brine (100 mL) and concentrated. The residue was filtered through a silica gel (140 g) column rinsing with methylene chloride (700 mL) and then ethyl acetate (700 mL). The ethyl acetate filtrate was concentrated to give 15 (5.34 g, 93%) as light yellow foamy solid, which was used without further purification.

39

Oxidative Cleavage of 1,2-diol of 15 to Give ((4S,5S)-5-(((2R,3S,4S)-2-(azidomethyl)-4-((1,3-dioxoisoindolin-2-yl)methyl)-3-(4-(phenylethynyl)phenyl)azetidin-1-yl)methyl)-2,2-dimethyl-1,3-dioxolane-4-carbaldehyde) 16

40

Converting 16 to (2-(((3aR,6aR,7R,8S,10aS)-2,2-dimethyl-7-(4-(phenylethynyl)phenyl)octahydro-5H-azeto[1,2-a][1,3]dioxolo[4,5-f][1,4]diazocin-8-yl)methyl)isoindoline-1,3-dione) 18 Using Aza-Wittig Reaction Followed by Reduction

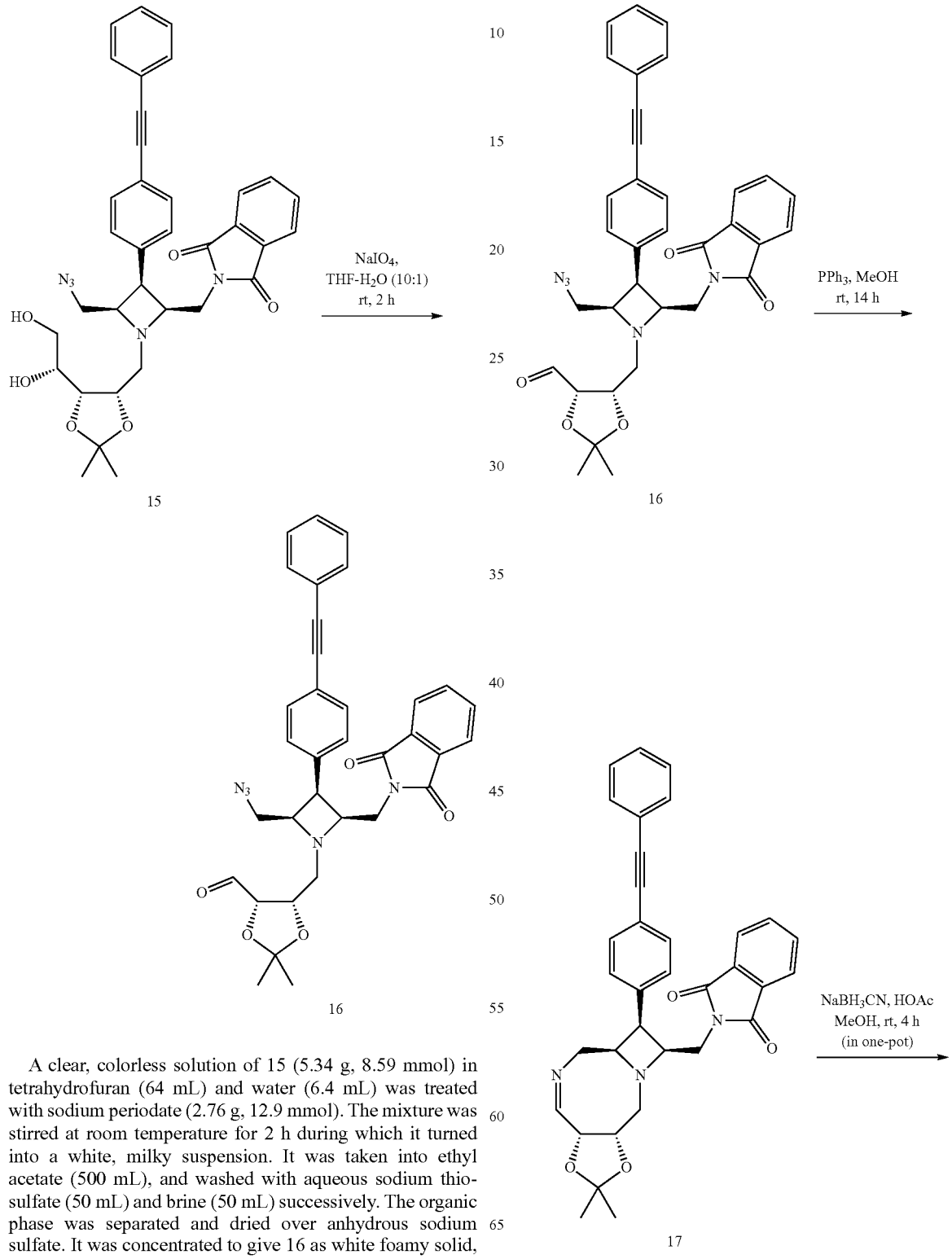

A clear, colorless solution of 15 (5.34 g, 8.59 mmol) in tetrahydrofuran (64 mL) and water (6.4 mL) was treated with sodium periodate (2.76 g, 12.9 mmol). The mixture was stirred at room temperature for 2 h during which it turned into a white, milky suspension. It was taken into ethyl acetate (500 mL), and washed with aqueous sodium thiosulfate (50 mL) and brine (50 mL) successively. The organic phase was separated and dried over anhydrous sodium sulfate. It was concentrated to give 16 as white foamy solid, which was used without purification.

41

-continued

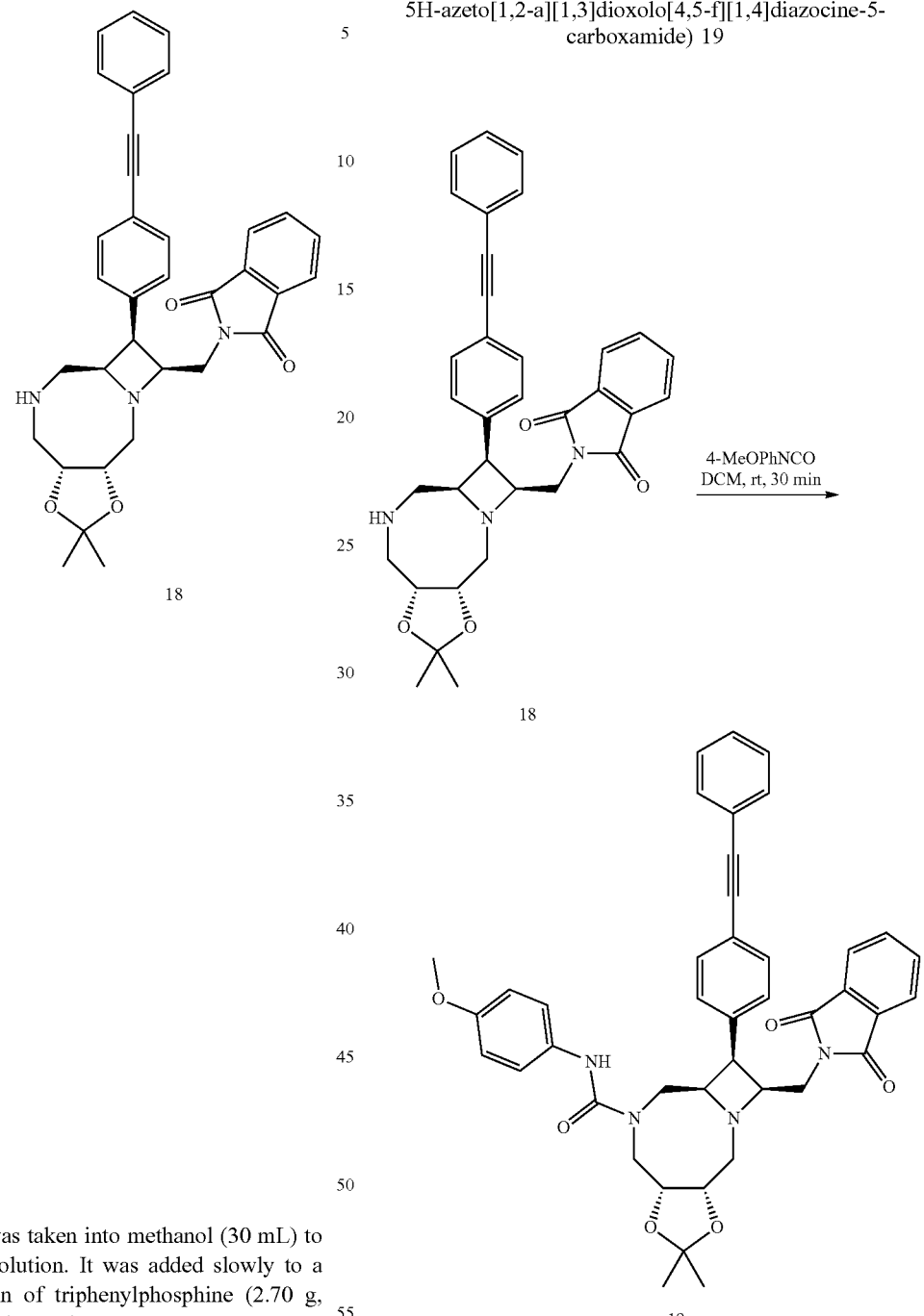

18

The above crude 16 was taken into methanol (30 mL) to give a clear, colorless solution. It was added slowly to a stirring white suspension of triphenylphosphine (2.70 g, 10.3 mmol) in methanol (50 mL) at room temperature over 8 h during which the mixture turned into a colorless, homogeneous solution. The solution was further stirred at the temperature for 6 h before acetic acid (2.46 mL, 43.0 mmol) and sodium cyanoborohydride (0.648 g, 10.3 mmol) were added. The mixture was stirred at the temperature for 4 h and then concentrated. The residue was taken into ethyl acetate (400 mL), washed with 1 M sodium hydroxide (40 mL) and brine (40 mL). The organic phase was dried over anhydrous sodium sulfate and concentrated to give crude 18 as colorless gum.

42

Converting 18 to ((3aR,6aR,7S,8S,10aS)-8-((1,3-dioxoisoindolin-2-yl)methyl)-N-(4-methoxyphenyl)-2,2-dimethyl-7-(4-(phenylethynyl)phenyl)octahydro-5H-azeto[1,2-a][1,3]dioxolo[4,5-f][1,4]diazocine-5-carboxamide) 19

18

19

The above crude 18 was taken into dichloromethane (57 mL) and treated with 4-methoxyphenyl isocyanate (1.34 mL, 10.3 mmol). The mixture was maintained at room temperature for 30 min and then concentrated. The residue was crystalized in a mixed solvent of isopropanol/acetonitrile (1:1, 100 mL) to give 19 (1.60 g) as white solid. The mother liquor was concentrated and purified using silica gel column chromatography eluting with 50 to 60% ethyl acetate in heptane to give additional 19 (1.0 g, combined 43% yield from 12).

¹H NMR (400 MHz, DMF-d₇) δ 8.44 (s, 1H), 7.88 (s, 4H), 7.74 (d, J=8.2 Hz, 2H), 7.64-7.61 (m, 4H), 7.51-7.44 (m, 3H), 7.37-7.33 (m, 2H), 6.87-6.83 (m, 2H), 4.50-4.47 (m, 1H), 4.34-4.29 (m, 1H), 4.08 (br dd, J=16.0, 5.0 Hz, 1H), 3.97 (br dd, J=16.0, 2.8 Hz, 1H), 3.87-3.65 (m, 6H), 3.75 (s, 3H), 3.52 (dd, J=14.0, 4.6 Hz, 1H), 3.48 (s, 1H), 3.10 (br t, J=2.1 Hz, 1H), 1.39 (s, 3H), 1.37 (s, 3H); ¹³C NMR (75 MHz, DMF-d₇) δ 168.9, 163.3, 157.5, 156.1, 138.5, 135.5, 135.0, 133.1, 132.6, 132.4, 132.3, 129.9, 129.8, 124.1, 124.1, 122.4, 122.1, 114.8, 108.1, 90.5, 90.5, 78.9, 77.4, 68.0, 66.5, 59.0, 56.1, 50.7, 47.4, 45.0, 39.7, 28.9, 26.3.

Hydrolysis of the Phthalimide of 19 to Give ((3aR, 6aR,7S,8S,10aS)-8-(aminomethyl)-N-(4-methoxyphenyl)-2,2-dimethyl-7-(4-(phenylethynyl)phenyl) octahydro-5H-azeto[1,2-a][1,3]dioxolo[4,5-f][1,4] diazocine-5-carboxamide) 20

A white suspension of 19 (2.30 g, 3.30 mmol) in methanol (23 mL) was treated with ethanolamine (2.00 mL, 33.0 mmol). The mixture was stirred at 55° C. for 12 h and then refluxed for 12 h during which it turned into a homogeneous solution. It was treated with ethanolamine (1.50 mL, 24.8 mmol) and refluxed for 24 h. The solution was concentrated to give a colorless gum, which was taken into dichloromethane (300 mL), washed with water (50 mL×2), brine (50 mL), and dried over anhydrous sodium sulfate. It was concentrated to give crude 20 as white waxy solid, which was used without purification.

Reductive Amination and Acetonide Removal of 20 to Give ((3S,4R,8R,9S,10S)-10-((dimethylamino) methyl)-3,4-dihydroxy-N-(4-methoxyphenyl)-9-(4-(phenylethynyl)phenyl)-1,6-diazabicyclo[6.2.0]decane-6-carboxamide) 22

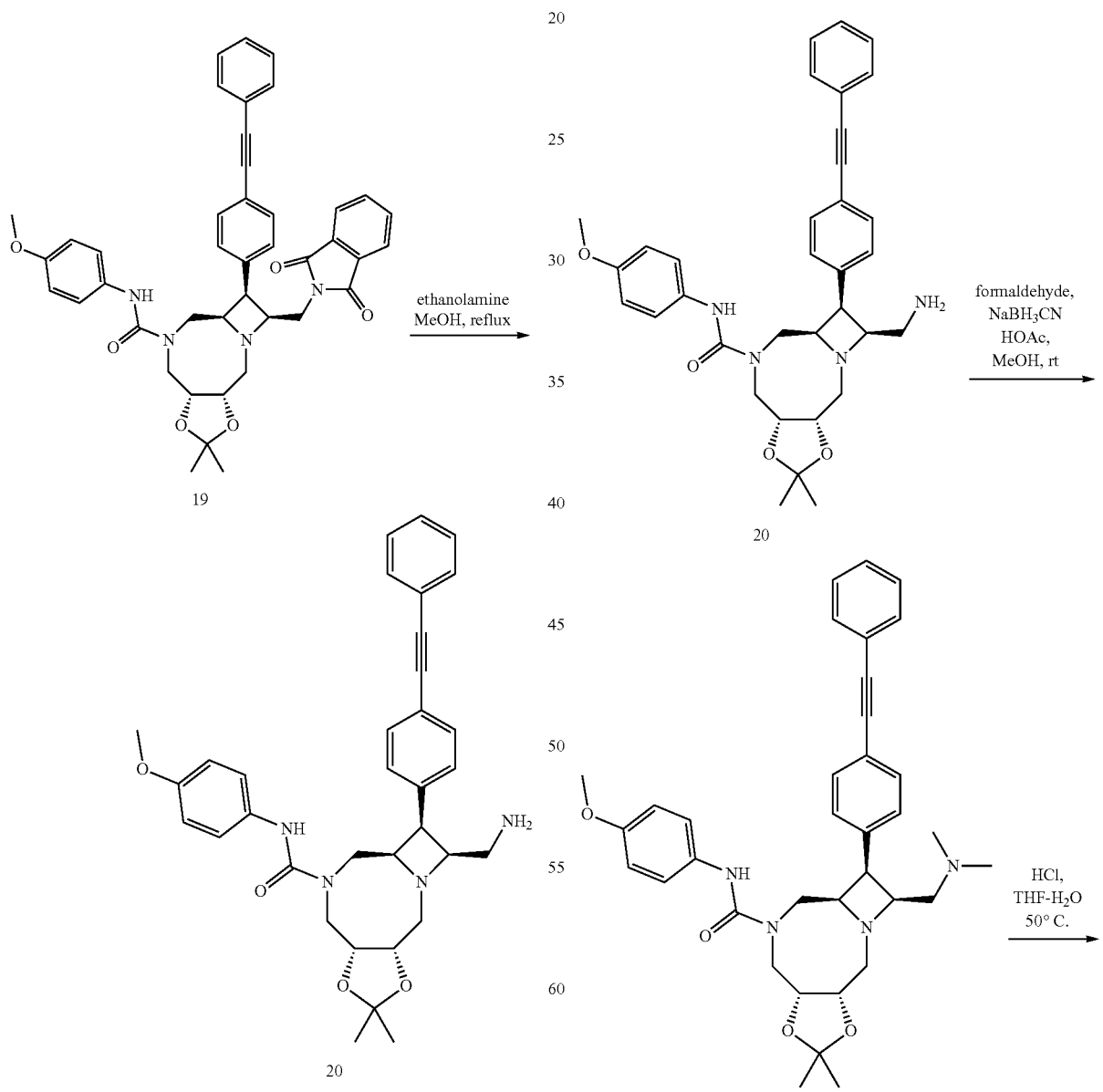

-continued

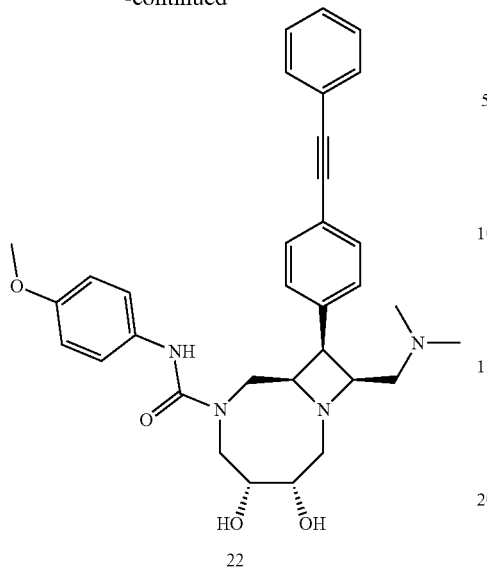

22

The above crude 20 was taken into methanol (18.7 mL) to give a suspension, which was treated with formaldehyde (37%, 3.69 mmol, 49.5 mmol), acetic acid (1.13 mL, 19.8 mmol) and sodium cyanoborohydride (0.622 g, 9.90 mmol). The mixture was stirred at room temperature for 2 h before it was taken into ethyl acetate (150 mL), washed with aqueous sodium bicarbonate (10 mL), brine (10 mL), dried over anhydrous sodium sulfate, and concentrated. The residue was passed through a pad of silica gel eluting with 15% methanol in dichloromethane, and concentrated to give crude ((3aR,6aR,7S,8S,10aS)-8-((dimethylamino)methyl)-N-(4-methoxyphenyl)-2,2-dimethyl-7-(4-(phenylethynyl)phenyl)octahydro-5H-azeto[1,2-a][1,3]dioxolo[4,5-f][1,4]diazocine-5-carboxamide) 21 as colorless gum, which was used without further purification.

The above crude 21 was taken into a mixed solvent of tetrahydrofuran (14 mL) and 1 M hydrochloric acid (14 mL, 14 mmol) to give a colorless solution, which was stirred at 50° C. for 12 h. It was taken into ethyl acetate (300 mL), washed with 1 M sodium hydroxide (50 mL), brine (50 mL), dried over anhydrous sodium sulfate, and concentrated. The residue was purified by silica gel column chromatography eluting with 20-30% methanol in dichloromethane (conditioned with 0.1% of 7 M ammonia in methanol) to give 22 (0.86 g, 52%) as white waxy solid.

$^1$H NMR (400 MHz, MeOH-$d_4$) δ 7.56-7.51 (m, 6H), 7.42-7.36 (m, 3H), 7.16 (d, J=9.0 Hz, 2H), 6.84 (d, J=8.9 Hz, 2H), 4.19 (dd, J=15.6, 6.6 Hz, 1H), 4.14-4.10 (m, 1H), 3.83-3.78 (m, 2H), 3.76 (s, 3H), 3.65 (dd, J=14.4, 7.6 Hz, 1H), 3.60 (br t, J=7.1 Hz, 1H), 3.40 (br t, J=8.8 Hz, 1H), 3.30 (d, J=10.5 Hz, 1H), 2.84 (dd, J=13.5, 9.2 Hz, 1H), 2.75 (dt, J=15.2, 3.0 Hz, 1H), 2.55 (dd, J=13.3, 8.6 Hz, 1H), 2.45 (dd, J=13.3, 2.4 Hz, 1H), 2.05 (s, 6H); $^{13}$C NMR (75 MHz, MeOH-$d_4$) δ 160.2, 157.3, 138.7, 134.2, 132.7, 132.5, 132.3, 129.7, 129.6, 124.8, 123.5, 123.3, 115.1, 90.5, 90.2, 77.0, 74.0, 71.3, 66.8, 58.2, 57.7, 56.0, 53.0, 52.1, 46.9, 46.0

Route B Synthesis

Reduction of Methyl 4-bromocinnamate 1 to Give 4-bromocinnamyl Alcohol 23

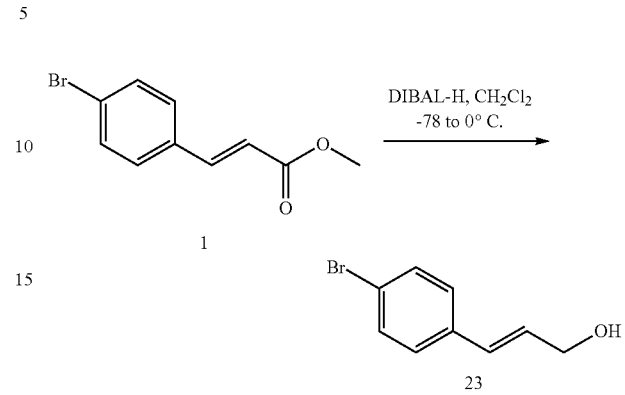

A 3 L three-neck round bottom flask was charged with methyl 4-bromocinnamate (1, 100 g, 414 mmol) and dichloromethane (1.1 L) to give a clear solution. It was cooled in a dry ice-acetone bath to give a milky mixture. It was treated with a solution of diisobutylaluminum hydride (25 wt % in toluene, 586 mL, 871 mmol) light greenish solution. The mixture was slowly allowed to −5° C. and carefully quenched with a solution of potassium sodium tartrate tetrahydrate (351 g, 1.24 mol) in water (800 mL) in an ice bath. The mixture was stirred at rt overnight, treated with water (2 L), and extracted with methyl tert-butyl ether (1 L×3). The combined organic phases were dried over anhydrous sodium sulfate and concentrated to give 4-bromocinnamyl alcohol (23, 87.5 g, 99%) as white solid.

$^1$H NMR (400 MHz, CDCl$_3$) δ 7.46-7.44 (m, 2H), 7.27-7.25 (m, 2H), 6.58 (d, J=16.0 Hz, 1H), 6.37 (dt, J=15.6, 5.5 Hz, 1H), 4.33 (dd, J=5.8, 1.5 Hz, 2H)

Bromination of 4-bromocinnamyl Alcohol 23 to Give 4-bromocinnamyl Bromide 24

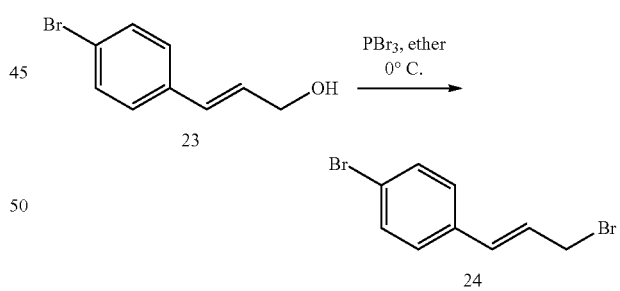

A 5 L three-neck round bottom flask was charged with 4-bromocinnamyl alcohol (23, 329 g, 1.54 mol) and diethyl ether (3 L). It was cooled to 5° C. using an ice bath during which the solution turned slightly cloudy. A solution of tribromophosphane (72.6 mL, 772 mmol) in diethyl ether (200 mL) was added dropwise this mixture while maintaining the internal temperature below 12° C. to give, at the end of addition, a mostly clear solution. The mixture was stirred for one hour in the ice bath before it was quenched by slow addition of a solution of sodium bicarbonate (133 g, 1.57 mol) in water (1.5 L). The organic phase was separated and washed with brine (300 mL). The aqueous phase was extracted with methyl tert-butyl ether (1 L×2). The combined organic phases were dried over anhydrous sodium sulfate and concentrated to give pure 24 (404 g, 95%) as white solid.

$^1$H NMR (400 MHz, CDCl$_3$) δ 7.48-7.45 (m, 2H), 7.25-7.24 (m, 2H), 6.59 (d, J=15.6 Hz, 1H), 6.40 (dt, J=15.6, 7.4 Hz, 1H), 4.15 (dt, J=7.8, 0.7 Hz, 2H)

Preparation of (ethyl (S,E)-2-((tert-butylsulfinyl)imino)acetate) 25

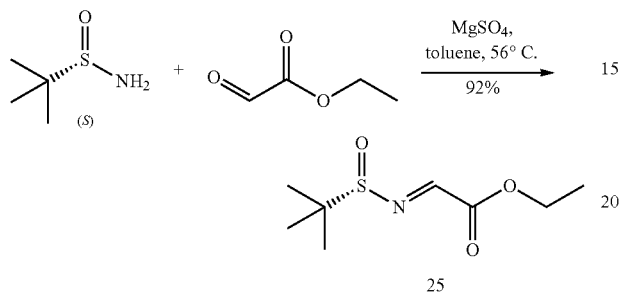

Zinc-Mediated Crotylation of 25 to Give (ethyl (2S,3S)-3-(4-bromophenyl)-2-(((S)-tert-butylsulfinyl)amino)pent-4-enoate) 26

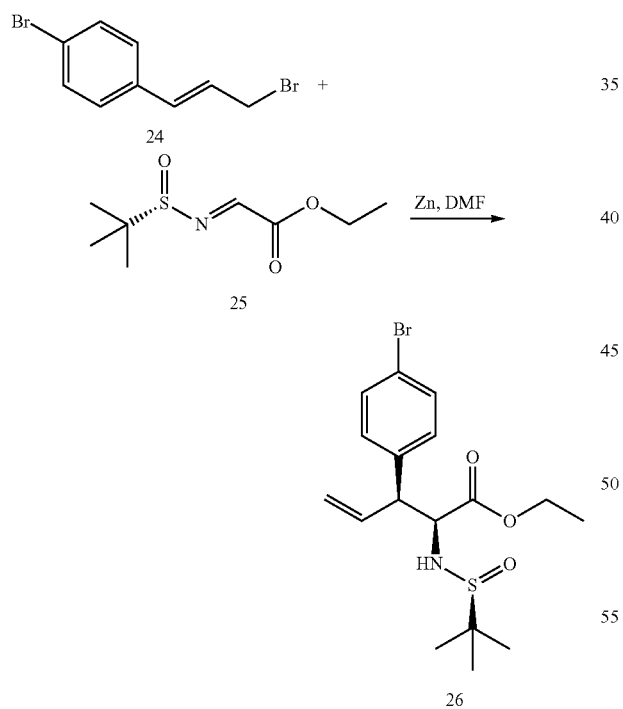

A 5 L three-neck round bottom flask was charged with 4-bromocinnamyl bromide (24, 175 g, 6363 mmol), 25 (87 g, 424 mmol) and N,N-dimethylformamide (1.3 L). The solution was sparged with nitrogen gas with stirring for 30 min. Zinc dust (55.4 g, 848 mmol) was added in portions while maintaining the internal temperature below 48 degree. The mixture turned green initially and then brown toward the end of addition. It was stirred at ambient temperature for 2 h before the reaction was quenched with water (1.3 L). The mixture was filtered through a pad of celite, rinsing with methyl tert-butyl ether. The filtrate was taken into water (1.3 L) and the aqueous phase was extracted with methyl tert-butyl ether (870 mL×2). The combined organic phases were concentrated and the concentrate was filtered through a pad of celite rinsing with small amount of methyl tert-butyl ether. The filtrate was concentrated and the residue was purified by silica gel column chromatography eluting with ethyl acetate in heptane to give 26 (111 g, 65.2%) as light yellow oil.

$^1$H NMR (400 MHz, CDCl$_3$) δ 7.44-7.40 (m, 2H), 7.05-7.03 (m, 2H), 6.05-5.96 (m, 1H), 5.17-5.11 (m, 2H), 4.20-4.12 (m, 3H), 3.91 (d, J=9.4 Hz, 1H), 3.67 (t, J=7.8 Hz, 1H), 1.25 (s, 3H)

Converting Sulfinamide 26 to (ethyl (2S,3S)-3-(4-bromophenyl)-2-((2-nitrophenyl)sulfonamido)pent-4-enoate) 27

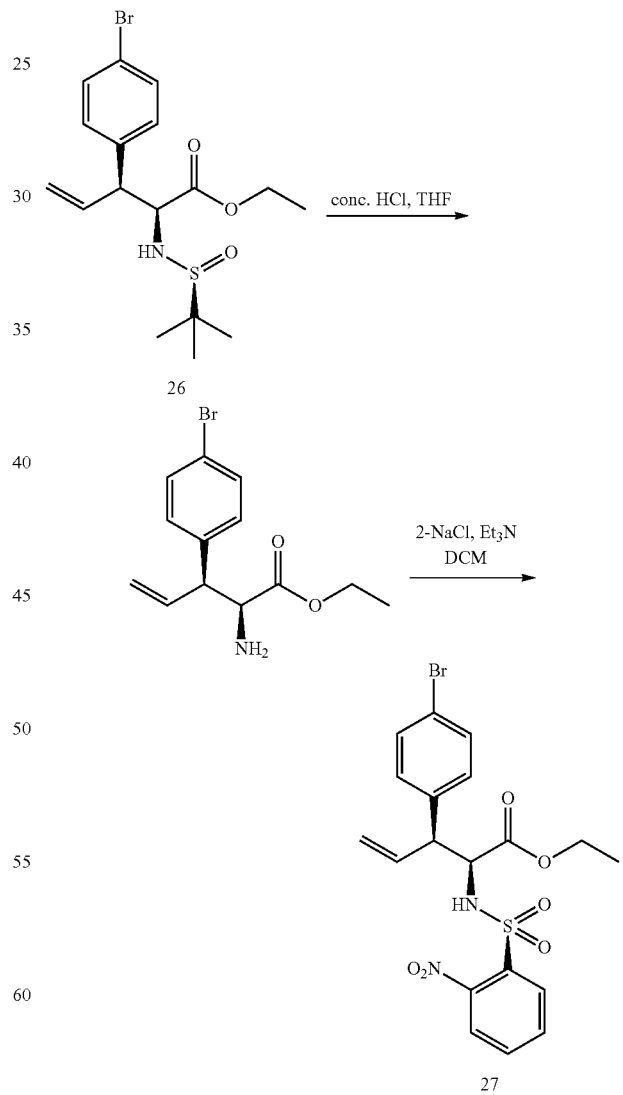

A solution of 26 (2.48 g, 5.30 mmol) in tetrahydrofuran (21 mL) was treated with concentrated hydrogen chloride (37%, 2.18 mL, 26.5 mmol) and stirred at room temperature for 2 h. The reaction was quenched with aq sodium bicarbonate (20 mL), followed by solid sodium bicarbonate till the mixture was no longer acidic. The mixture was extracted with methyl tert-butyl ether (200 mL×3), dried over anhydrous sodium sulfate, and concentrated to give a thick yellow oil.

It was taken into dichloromethane (16 mL), treated with 2-nitrobenzenesulfonyl chloride (1.29 g, 5.83 mmol) and triethylamine (1.11 mL, 7.95 mmol) to give an orange solution, which was stirred at room temperature overnight. The mixture was taken into methyl tert-butyl ether (200 mL) and washed with 1 M sodium hydroxide (30 mL). The aqueous phase was extracted with methyl tert-butyl ether (50 mL). The combined organic phases were dried over anhydrous sodium sulfate and concentrated. The residue was purified by silica gel column chromatography eluting with 15-40% ethyl acetate in heptane to give 27 (2.29 g, 89%) as light yellow gum.

$^1$H NMR (400 MHz, MeOH-d$_4$) δ 7.50-7.32 (m, 3H), 7.23-7.19 (m, 2H), 7.10-7.07 (m, 2H), 5.97-5.88 (m, 1H), 5.01 (dd, J=17.0, 1.0 Hz, 1H), 4.95 (dd, J=10.1, 1.3 Hz, 1H), 4.06 (d, J=10.5 Hz, 1H), 4.03-3.92 (m, 2H), 3.58 (t, J=9.8 Hz, 1H), 1.76 (t, J=7.0 Hz, 3H)

Iodolactonization of 27 and Azido-Substitution to Give (N-((3S,4S,5S)-5-(azidomethyl)-4-(4-bromophenyl)-2-oxotetrahydrofuran-3-yl)-2-nitrobenzenesulfonamide) 29

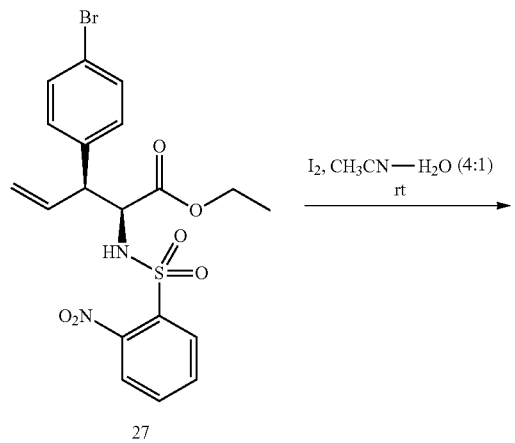

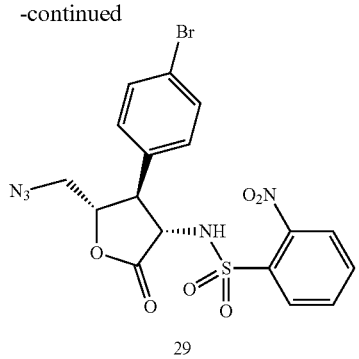

A solution of 27 (10.0 g, 20.7 mmol) in acetonitrile (80 mL) and water (3.2 mL) was treated with iodine (10.5 g, 41.3 mmol) to give a dark red solution, which was stirred at rt till all the starting material has been consumed. The reaction was quenched with excess aq sodium thiosulfate and stirred at rt till the mixture became light yellow. The mixture was taken into methyl tert-butyl ether, washed with brine, dried over anhydrous sodium sulfate and concentrated to give crude (N-((3S,4S,5S)-4-(4-bromophenyl)-5-(iodomethyl)-2-oxotetrahydrofuran-3-yl)-2-nitrobenzenesulfonamide) 28 (12 g) as white solid.

$^1$H NMR (400 MHz, CDCl$_3$) δ 7.89 (dd, J=8.1, 1.4 Hz, 1H), 7.81 (dd, J=8.0, 1.4 Hz, 1H), 7.72 (dt, J=7.8, 1.5 Hz, 1H), 7.62 (dt, J=7.8, 1.2 Hz, 1H), 7.44-7.41 (m, 2H), 7.15-7.12 (m, 2H), 6.25 (d, 9.0 Hz, 1H), 4.81 (dd, J=12.1, 9.0 Hz, 1H), 4.27-4.22 (m, 1H), 3.48-3.41 (m, 2H), 3.24 (dd, J=11.9, 4.9 Hz, 1H)

The crude 28 was taken into N,N-dimethylformamide (65 mL) and treated with sodium azide (2.02 g, 31.0 mmol) to give a yellow suspension, which was stirred at rt overnight. The mixture was taken into methyl tert-butyl ether, washed with water, brine, dried over anhydrous sodium sulfate, and concentrated. The residue was purified using silica gel column chromatography eluting with ethyl acetate in heptane to give 29 (7.90 g, 77%) as white solid.

$^1$H NMR (400 MHz, CDCl$_3$) δ 7.84 (dd, J=8.0, 0.9 Hz, 1H), 7.75 (dd, J=7.8, 1.2 Hz, 1H), 7.69 (dt, J=7.6, 1.3 Hz, 1H), 7.57 (dt, J=7.6, 1.2 Hz, 1H), 7.34 (d, J=8.6 Hz, 2H), 7.09 (d, J=8.6 Hz, 2H), 6.46 (d, J=9.0 Hz, 1H), 4.79 (dd, J=12.1, 9.0 Hz, 1H), 4.58-4.53 (m, 1H), 3.63-3.53 (m, 2H), 3.38 (dd, J=13.9, 4.9 Hz, 1H)

Reduction of 29 to Give (N-((2S,3S,4S)-5-azido-3-(4-bromophenyl)-1,4-dihydroxypentan-2-yl)-2-nitrobenzenesulfonamide) 30

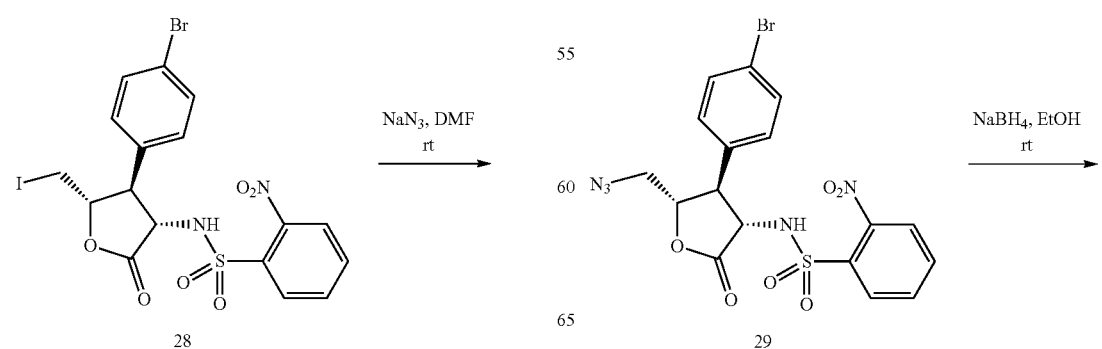

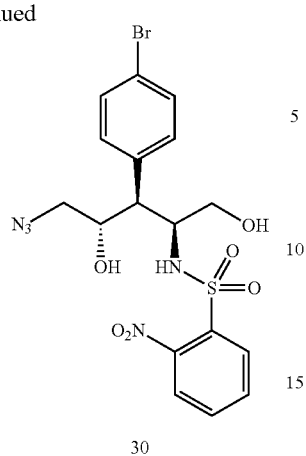

30

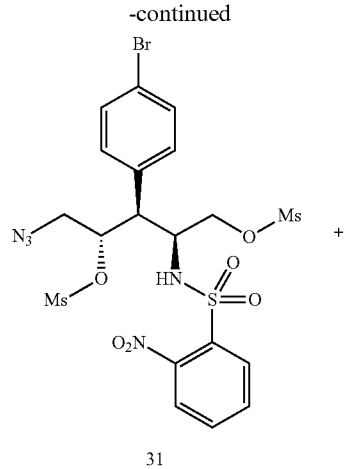

31

A yellow solution of 29 (9.10 g, 18.3 mmol) in ethanol (80 mL) was treated with sodium borohydride (1.04 g, 27.5 mmol) in portions during which the mixture turned dark purple. The reaction was stirred at rt for 1 h before it was quenched with 1 M HCl. The mixture taken into methyl tert-butyl ether, washed with water, brine, dried over anhydrous sodium sulfate and concentrated. The residue was purified using silica gel column chromatography eluting with 50-80% ethyl acetate in heptane to give 30 (8.20 g, 89%) as white solid.

$^1$H NMR (400 MHz, CDCl$_3$) δ 8.17-8.15 (m, 1H), 7.92-7.89 (m, 1H), 7.80-7.75 (m, 2H), 7.48 (d, J=8.6 Hz, 2H), 7.10 (d, J=8.2 Hz, 2H), 5.45 (d, J=9.0 Hz, 1H), 4.41-4.37 (m, 1H), 4.16-4.11 (m, 1H), 3.72 (brs, 1H), 3.44 (dd, J=11.4, 5.5 Hz, 1H), 3.30 (dd, J=11.3, 7.0 Hz, 1H), 3.23 (dd, J=12.9, 2.7 Hz, 1H), 3.00-2.91 (m, 2H)

Converting 30 to Azetidine (2-(((2S,3S,4R)-4-(azidomethyl)-3-(4-bromophenyl)-1-((2-nitrophenyl)sulfonyl)azetidin-2-yl)methyl)isoindoline-1,3-dione) 32 by Bis-Mesylation and Tandem N-Nucleophilic Substitution

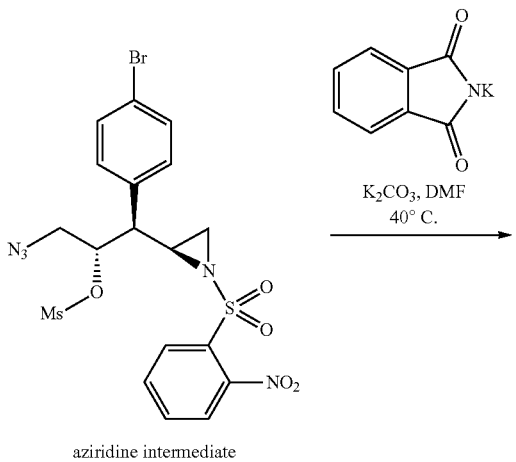

aziridine intermediate

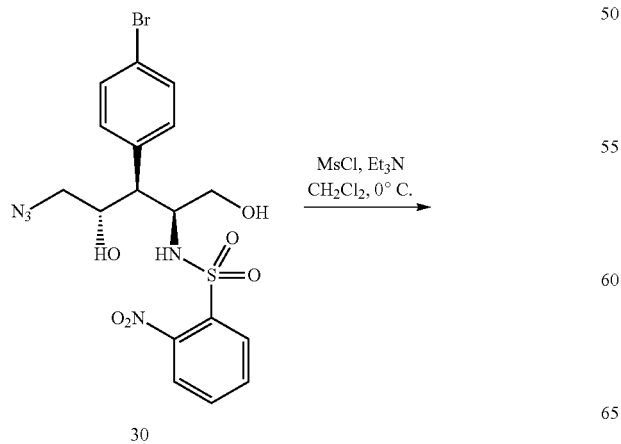

30

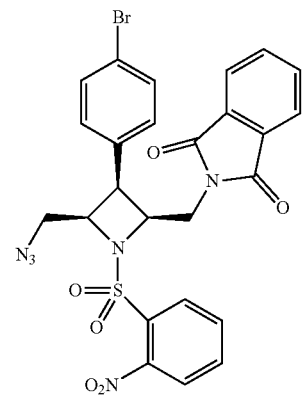

32

A solution of 30 (5.37 g, 10.7 mmol) and triethylamine (5.98 mL, 42.9 mmol) in dichloromethane (50 mL) was cooled to 0° C. and treated with methanesulfonyl chloride (2.08 mL, 26.8 mmol) dropwise. The light yellow cloudy mixture was stirred at the temperature for 2 h before the reaction was quenched with aqueous sodium bicarbonate. The mixture was extracted with ethyl acetate, washed with water and brine. The organic phase was dried over anhydrous sodium sulfate and concentrated to give a crude consisting of 31 and the aziridine intermediate.

The residue was taken into N,N-dimethylformamide (35 mL), treated with potassium carbonate (4.45 g, 32.2 mmol), potassium phthalimide (2.39 g, 12.9 mmol), and stirred at rt for 84 h. The mixture was taken into ethyl acetate, washed with water, brine, dried over anhydrous sodium sulfate, and concentrated. The residue was purified using silica gel column chromatography eluting with ethyl acetate in heptane to give 32 (4.92 g, 75%) as white solid.
$^1$H NMR (400 MHz, CDCl$_3$) δ 8.14 (dd, J=7.9, 1.6 Hz, 1H), 7.83-7.70 (m, 7H), 7.58 (d, J=8.6 Hz, 2H), 7.33 (d, J=8.2 Hz, 2H), 4.91 (dd, J=14.9, 6.7 Hz, 1H), 4.56-4.50 (m, 1H), 4.18 (dd, J=17.7, 6.0 Hz, 1H), 3.77-3.68 (m, 3H), 3.55 (dd, J=12.7, 9.6 Hz, 1H)

Converting 32 to (2-(((2S,3S,4R)-4-(azidomethyl)-3-(4-bromophenyl)-1-(((4S,5R)-5-((R)-1,2-dihydroxyethyl)-2,2-dimethyl-1,3-dioxolan-4-yl)methyl)azetidin-2-yl)methyl)isoindoline-1,3-dione) 35 by Deprotection and Reductive Amination

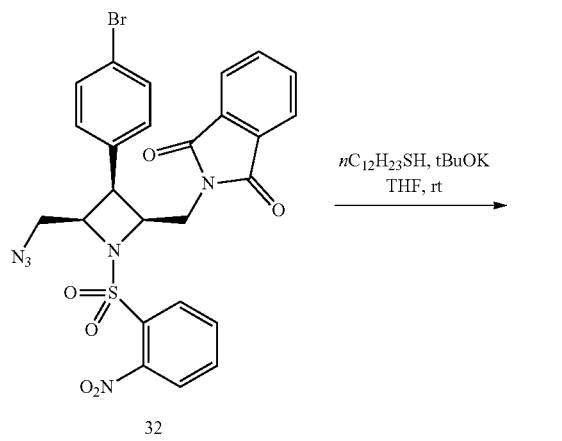

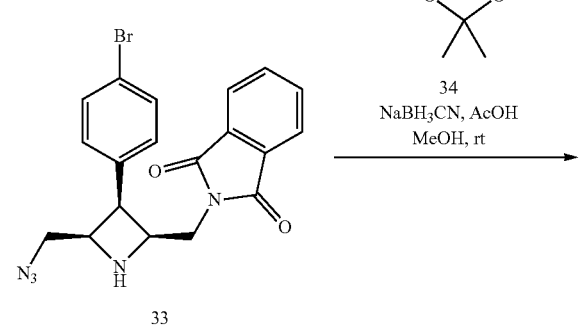

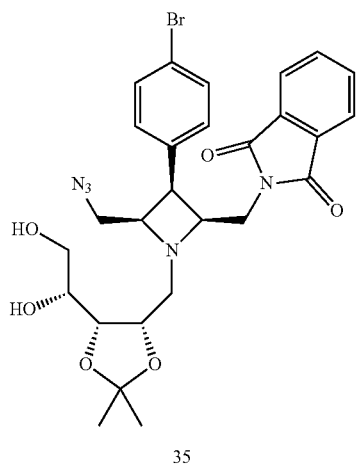

A solution of 32 (1.35 g, 2.21 mmol) and 1-dodecanethiol (0.635 mL, 2.65 mmol) in tetrahydrofuran (10 mL) was treated with a solution of potassium tert-butoxide (1 M in tetrahydrofuran, 2.65 mL, 2.65 mmol) dropwise at room temperature and then stirred for 5 h. The mixture was taken into ethyl acetate, washed with brine, dried over anhydrous sodium sulfate and concentrated to give crude (2-(((2S,3S,4R)-4-(azidomethyl)-3-(4-bromophenyl)azetidin-2-yl)methyl)isoindoline-1,3-dione) 33 as yellow gum.

A mixture of crude 33 (0.469 g, 1.10 mmol) and ((3aR,6R,6aR)-6-(hydroxymethyl)-2,2-dimethyltetrahydrofuro[3,4-d][1,3]dioxol-4-ol) 34 (0.29 g, 1.53 mmol) was taken into methanol (5 mL), treated with acetic acid (0.315 mL, 5.50 mmol), sodium cyanoborohydride (0.104 g, 1.65 mmol), and stirred at rt till the reaction was complete. The mixture was taken into ethyl acetate, washed with 1 M sodium hydroxide, brine, dried over anhydrous sodium sulfate and concentrated. The residue was purified using silica gel column chromatography eluting with methanol in dichloromethane to give 35 (365 mg, 55%) as colorless oil.

$^1$H NMR (400 MHz, CDCl$_3$) δ 7.77-7.74 (m, 2H), 7.71-7.67 (m, 2H), 7.52 (d, J=8.2 Hz, 2H), 7.19 (d, J=8.6 Hz, 2H), 6.11 (brs, 1H), 4.53-4.48 (m, 1H), 4.31 (dd, J=9.3, 6.2 Hz, 1H), 3.93-3.75 (m, 7H), 3.58 (dd, J=13.9, 7.3 Hz, 1H), 3.51-3.46 (m, 1H), 3.32-3.24 (m, 2H), 2.77 (dd, J=12.5, 3.9 Hz, 1H), 2.49 (brs, 1H), 1.41 (s, 3H), 1.33 (s, 3H)

Reductive Amination of 33 with ((3aR,6aR)-2,2-dimethyltetrahydrofuro[3,4-d][1,3]dioxol-4-ol) 36 to Give (2-(((2S,3S,4R)-4-(azidomethyl)-3-(4-bromophenyl)-1-(((4S,5R)-5-(hydroxymethyl)-2,2-dimethyl-1,3-dioxolan-4-yl)methyl)azetidin-2-yl)methyl)isoindoline-1,3-dione) 37

Oxidative Cleavage of 35 to Give ((4S,5S)-5-(((2R,3S,4S)-2-(azidomethyl)-3-(4-bromophenyl)-4-((1,3-dioxoisoindolin-2-yl)methyl)azetidin-1-yl)methyl)-2,2-dimethyl-1,3-dioxolane-4-carbaldehyde) 38

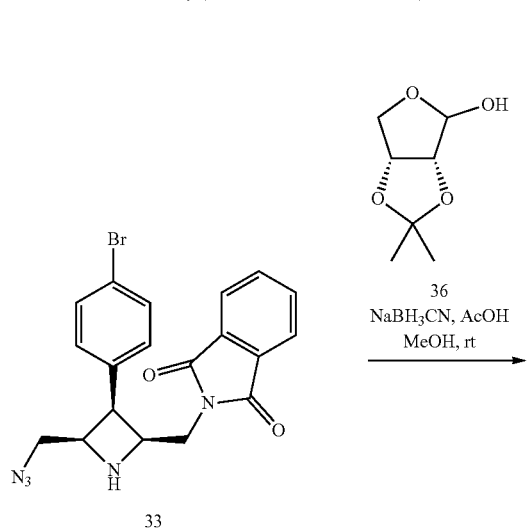

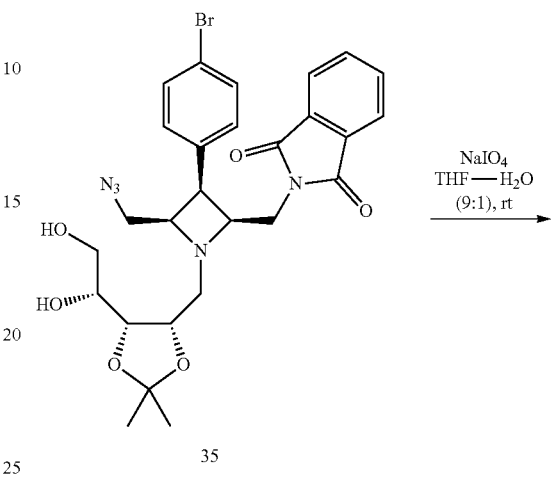

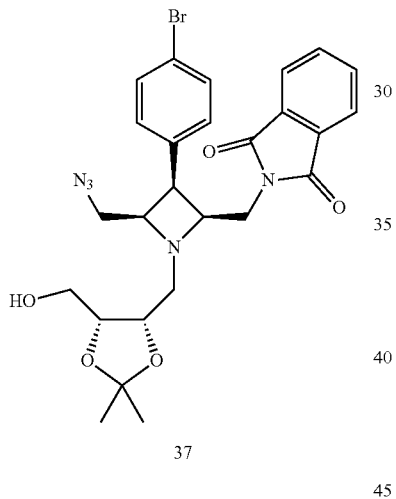

Crude 35 (2.72 g, 6.38 mmol) and 36 (1.53 g, 9.57 mmol) were taken into methanol (40 mL), acetic acid (1.83 mL, 31.9 mmol), and treated with sodium cyanoborohydride (0.601 g, 9.57 mmol). The mixture was stirred at rt till the reaction was complete. The mixture was taken into methyl tert-butyl ether (500 mL), washed with 1 M sodium hydroxide (50 mL) and brine (50 mL). The aqueous phase was back extracted with methyl tert-butyl ether (100 mL×2). The combined organic phase was dried over anhydrous sodium sulfate and concentrated. The residue was purified with silica gel column chromatography eluting with methanol in dichloromethane (conditioned with 70 mM of ammonia) to give 37 (2.34 g, 64%) as white foamy solid.

$^1$H NMR (400 MHz, CDCl$_3$) δ 7.75-7.71 (m, 2H), 7.68-7.64 (m, 2H), 7.48-7.45 (m, 2H), 7.23-7.21 (m, 2H), 4.43-4.34 (m, 2H), 4.01 (brs, 1H), 3.81-3.66 (m, 6H), 3.50 (dd, J=13.7, 6.6 Hz, 1H), 3.42 (dd, J=12.7, 6.5 Hz, 1H), 3.21 (dd, 12.7, 6.5 Hz, 1H), 3.08 (dd, 12.9, 7.8 Hz, 1H), 2.76 (dd, J=12.9, 5.1 Hz, 1H), 1.41 (s, 3H), 1.31 (s, 3H)

A solution of 35 (2.73 g, 4.55 mmol) in tetrahydrofuran (33 mL) and water (3.6 mL) was treated with sodium periodate (1.46 g, 6.82 mmol) and stirred at rt for 2 h to give a white suspension. The mixture was taken into methyl tert-butyl ether (500 mL), washed with aqueous sodium thiosulfate (100 mL) and aqueous sodium bicarbonate (100 mL). The combined aqueous phases were back extracted with methyl tert-butyl ether (150 mL×2). The combined organic phase was dried over anhydrous sodium sulfate and concentrated to give 38 as colorless gum, which was used without purification.

$^1$H NMR (400 MHz, CDCl$_3$) δ 9.79 (d, J=2.7 Hz, 1H), 7.78-7.75 (m, 2H), 7.71-7.68 (m, 2H), 7.52-7.49 (m, 2H), 7.31-7.29 (m, 2H), 4.54-4.51 (m, 1H), 4.47-4.44 (m, 2H), 3.79-3.3.61 (m, 4H), 3.46-3.40 (m, 2H), 3.21-3.19 (m, 1H), 2.96 (dd, J=13.7, 4.7 Hz, 1H), 2.80 (dd, J=13.7, 5.5 Hz, 1H), 1.60 (s, 3H), 1.41 (s, 3H)

Oxidation of 37 to Give 38

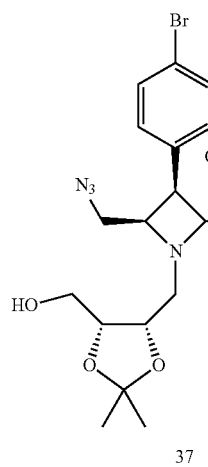

37

Aza-Wittig Reaction of 38 and Subsequent Reduction to Give (2-(((3aR,6aR,7R,8S,10aS)-7-(4-bromophenyl)-2,2-dimethyloctahydro-5H-azeto[1,2-a][1,3]dioxolo[4,5-f][1,4]diazocin-8-yl)methyl)isoindoline-1,3-dione) 40

38

39

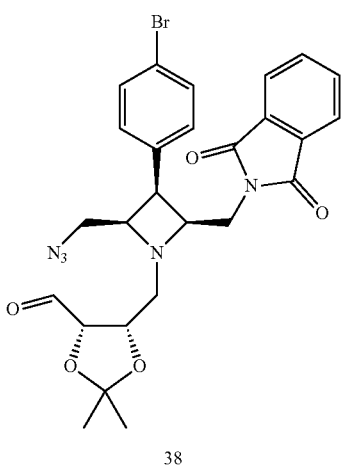

38

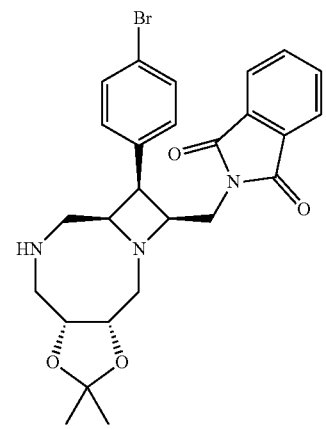

40

A solution of 37 (900 mg, 1.58 mmol) in dichloromethane (10 mL) was treated with Dess Martin periodinane (803 mg, 1.89 mmol) and stirred at rt for 3 h. The mixture was taken into ethyl acetate, washed with aq sodium thiosulfate, 1 M sodium hydroxide, brine, dried over anhydrous sodium sulfate, and concentrated to give 38 as colorless gum, which was used without purification.

To a suspension of triphenylphosphane (1.79 g, 6.82 mmol) in methanol (13 mL) was slowly added a solution of the crude 38 in methanol (39 mL) and tetrahydrofuran (7.8 mL) over 12 h to give a clear solution. After an additional 3 h, the solution was treated with acetic acid (0.78 mL, 13.6 mmol) and sodium cyanoborohydride (0.343 g, 5.46 mmol), and stirred for 3 h. The mixture was taken into methyl tert-butyl ether, washed with 1 M sodium hydroxide, brine, dried over anhydrous sodium sulfate and concentrated. The residue was purified by silica gel column chromatography eluting with ethyl acetate to give 40 (1.88 g, 79%) as white solid.

$^1$H NMR (400 MHz, CDCl$_3$) δ 7.81-7.77 (m, 2H), 7.71-7.64 (m, 2H), 7.46-7.44 (m, 2H), 7.40-7.38 (m, 2H), 4.87 (brs, 3H), 4.39-4.34 (m, 1H), 4.28-4.24 (m, 1H), 3.75 (dd, J=14.0, 5.5 Hz, 1H), 3.70-3.65 (m, 1H), 3.60-3.55 (m, 2H), 3.47 (dd, J=14.2, 5.3 Hz, 1H), 3.28 (dd, J=Hz, 1H), 3.27 (dd, J=14.6, 9.8 Hz, 1H), 3.08 (dd, J=14.7, 2.2 Hz, 1H), 2.90 (dd, J=13.2, 4.3 Hz, 1H), 2.79 (dd, J=13.6, 8.6 Hz, 1H), 2.71-2.60 (m, 2H), 1.36 (s, 3H), 1.32 (s, 3H)

Converting 40 to ((3aR,6aR,7S,8S,10aS)-7-(4-bromophenyl)-8-((1,3-dioxoisoindolin-2-yl)methyl)-N-(4-methoxyphenyl)-2,2-dimethyloctahydro-5H-azeto[1,2-a][1,3]dioxolo[4,5-f][1,4]diazocine-5-carboxamide) 41

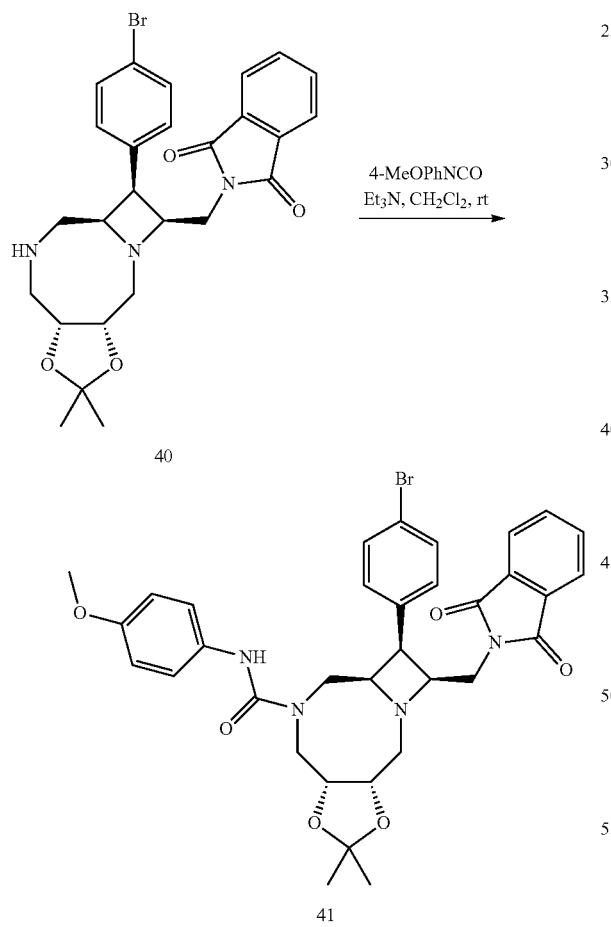

40

4-MeOPhNCO
Et$_3$N, CH$_2$Cl$_2$, rt

41

A solution of 40 (70 mg, 0.133 mmol) in dichloromethane (1.5 mL) was treated with 4-methoxyphenyl isocyanate (0.026 mL, 0.199 mmol), triethylamine (0.028 mL, 0.199 mL), and maintained at rt for 2 h. The mixture was concentrated and the residue was purified using silica gel column chromatography eluting with ~60% ethyl acetate in heptane to give 41 (67 mg, 75%) as white solid.

$^1$H NMR (400 MHz, CDCl$_3$) δ 8.35 (s, 1H), 7.85-7.80 (m, 2H), 7.73-7.69 (m, 2H), 7.51-7.45 (m, 4H), 7.23-7.19 (m, 2H), 6.85-6.80 (m, 2H), 4.38 (d, J=16.8 Hz, 1H), 4.29 (brs, 2H), 4.16-4.10 (m, 1H), 3.86-3.77 (m, 2H), 3.77 (s, 3H), 3.65-3.47 (m, 4H), 2.79-2.73 (m, 1H), 2.64-2.61 (m, 2H), 1.44 (s, 3H), 1.41 (s, 3H)

Hydrolysis of Acetonide 41 to Give ((3S,4R,8R,9S,10S)-9-(4-bromophenyl)-10-((1,3-dioxoisoindolin-2-yl)methyl)-3,4-dihydroxy-N-(4-methoxyphenyl)-1,6-diazabicyclo[6.2.0]decane-6-carboxamide) 42

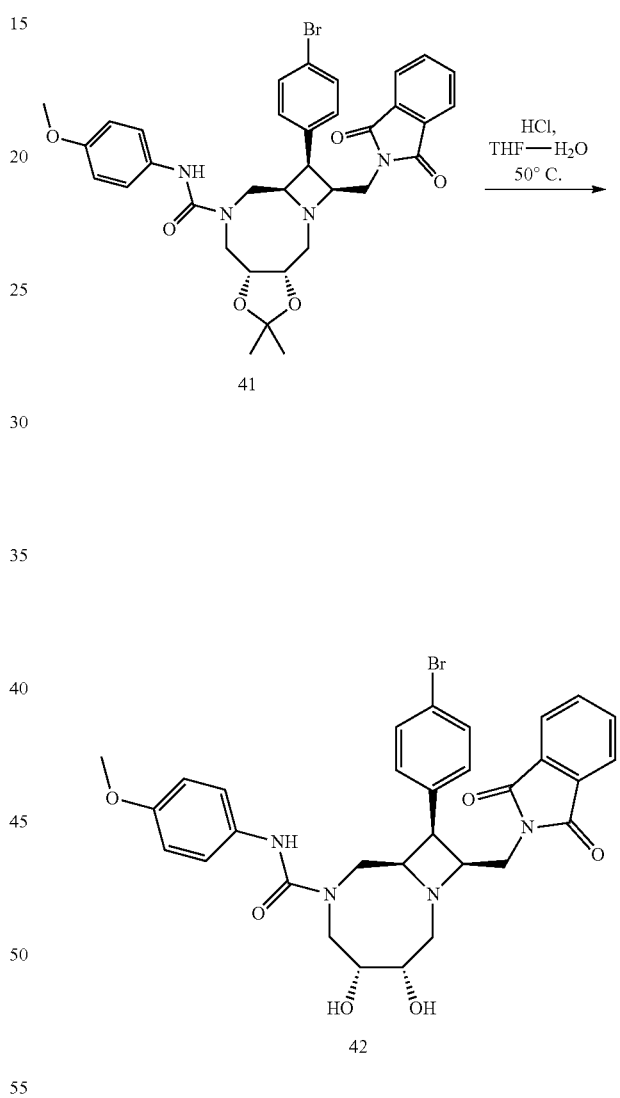

41

HCl,
THF—H$_2$O
50° C.

42

A solution of 41 (5.0 mg, 0.0074 mmol) in tetrahydrofuran (1 mL) and 1 M HCl (1 mL) was stirred at 50° C. for 3 h. The solution was concentrated and the residue purified by reverse phase preparative HPLC to give 42 (3.8 mg, 81%) as white solid.

$^1$H NMR (400 MHz, CD$_3$OD) δ 7.79-7.73 (m, 4H), 7.52-7.46 (m, 4H), 7.11-7.07 (m, 2H), 6.80-6.76 (m, 2H), 4.14 (dd, J=15.5, 6.5 Hz, 1H), 4.08-4.07 (m, 1H), 3.82-3.68 (m, 4H), 3.71 (s, 3H), 3.33-3.27 (m, 2H), 2.82-2.73 (m, 2H), 2.82-2.73 (m, 2H), 2.67-2.63 (m, 1H)

42 can be converted into compound 22 according to previously described procedures. See, e.g., pages 53-55 of WO 2018/175385, wholly incorporated by reference herein. This process is shown in brief form as follows:

Hydrolysis of o-Nitrophenylsulfonamide of 12 Using Thioglycolic Acid to Give 13

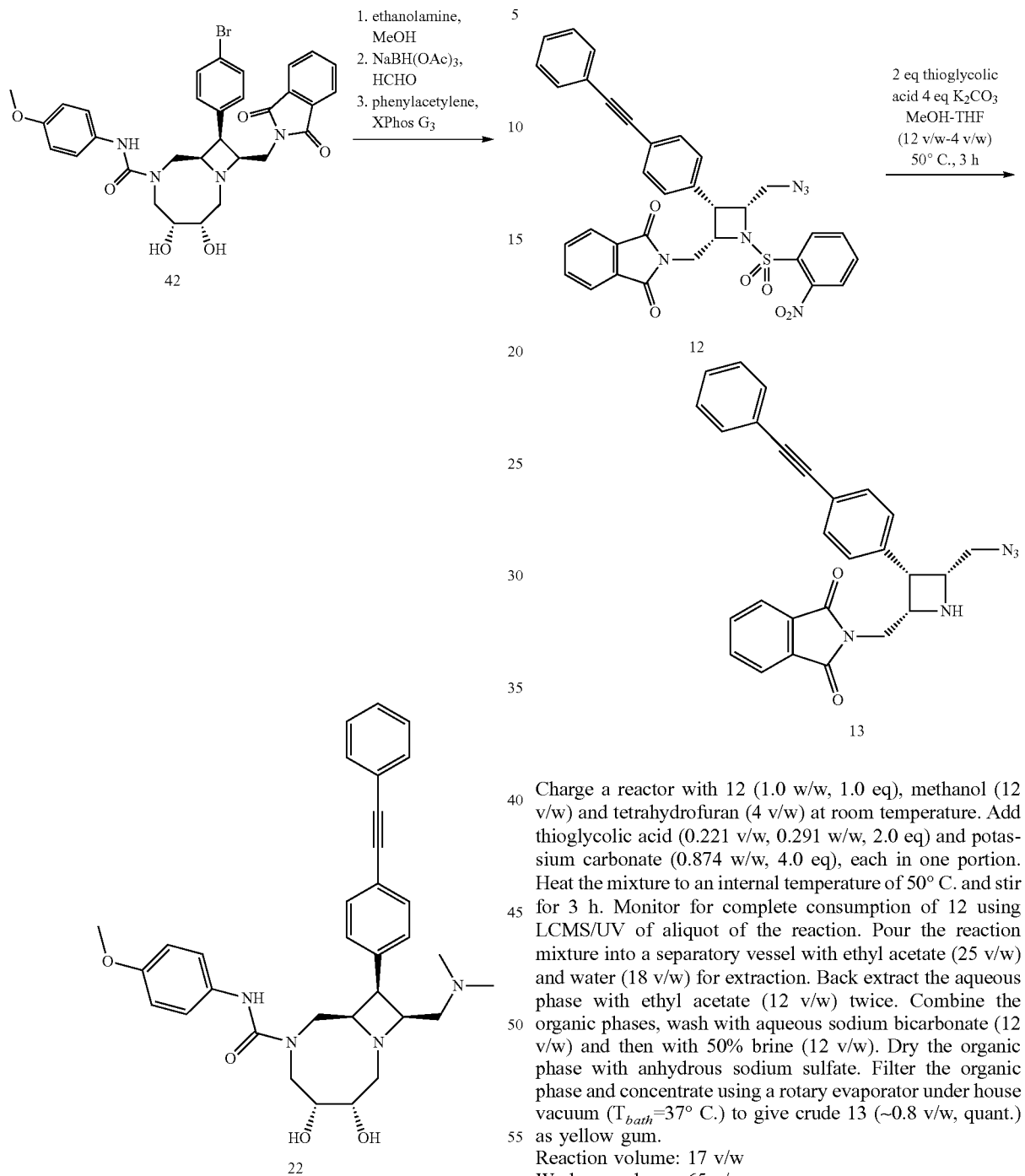

Figure 2:
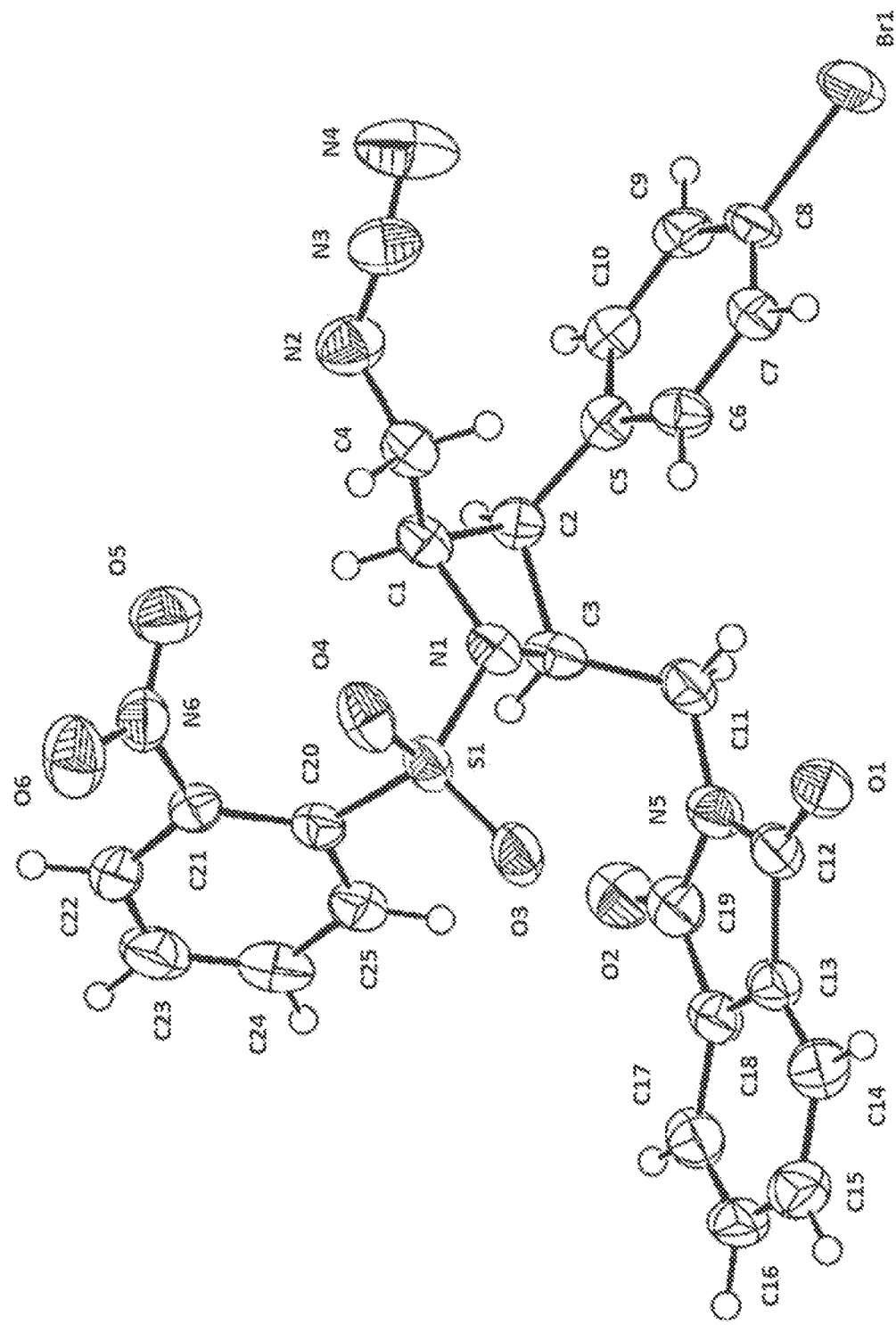
FIG. 2 shows an ORTEP projection for Compound 32.

The structures for compounds 5 and 32 were confirmed by X-ray crystallography. ORTEP projections for compounds 5 and 32 are provided in FIG. 1 and FIG. 2, respectively. ORTEP is an acronym for Oak Ridge Thermal Ellipsoid Plot, which is a representation of molecular structure as determined by X-ray diffraction.

Further procedures that may be combined with the above procedures or used independently are presented below.

Charge a reactor with 12 (1.0 w/w, 1.0 eq), methanol (12 v/w) and tetrahydrofuran (4 v/w) at room temperature. Add thioglycolic acid (0.221 v/w, 0.291 w/w, 2.0 eq) and potassium carbonate (0.874 w/w, 4.0 eq), each in one portion. Heat the mixture to an internal temperature of 50° C. and stir for 3 h. Monitor for complete consumption of 12 using LCMS/UV of aliquot of the reaction. Pour the reaction mixture into a separatory vessel with ethyl acetate (25 v/w) and water (18 v/w) for extraction. Back extract the aqueous phase with ethyl acetate (12 v/w) twice. Combine the organic phases, wash with aqueous sodium bicarbonate (12 v/w) and then with 50% brine (12 v/w). Dry the organic phase with anhydrous sodium sulfate. Filter the organic phase and concentrate using a rotary evaporator under house vacuum ($T_{bath}$=37° C.) to give crude 13 (~0.8 v/w, quant.) as yellow gum.
Reaction volume: 17 v/w
Work-up volume: 65 v/w
Expected yield (%): quantitative
Maximum scale: 20 g of 12
$^1$H NMR (400 MHz, CDCl$_3$) δ 7.84-7.82 (m, 2H), 7.72-7.67 (m, 2H), 7.62-7.52 (m, 6H), 7.39-7.32 (m, 3H), 4.50 (dt, J=7.6, 4.5 Hz, 1H), 4.25 (dd, J=14.1, 7.0 Hz, 1H), 3.91 (dd, J=14.3, 7.8 Hz, 1H), 3.79 (t, J=7.6 Hz, 1H), 3.53 (dd, J=14.2, 4.4 Hz, 1H), 3.35 (dd, J=12.6, 7.1 Hz, 1H), 3.20 (dd, J=12.6, 6.6 Hz, 1H); $^{13}$C NMR (75 MHz, CDCl$_3$) δ 168.2, 135.6, 134.3, 134.0, 132.0, 131.6, 131.6, 130.6, 128.4, 128.3, 123.3, 122.5, 89.9, 89.2, 57.5, 57.2, 52.0, 46.7, 40.2

Reductive Amination of 13 Using 14 to Give 15.HCl (HCl Salt of 15)

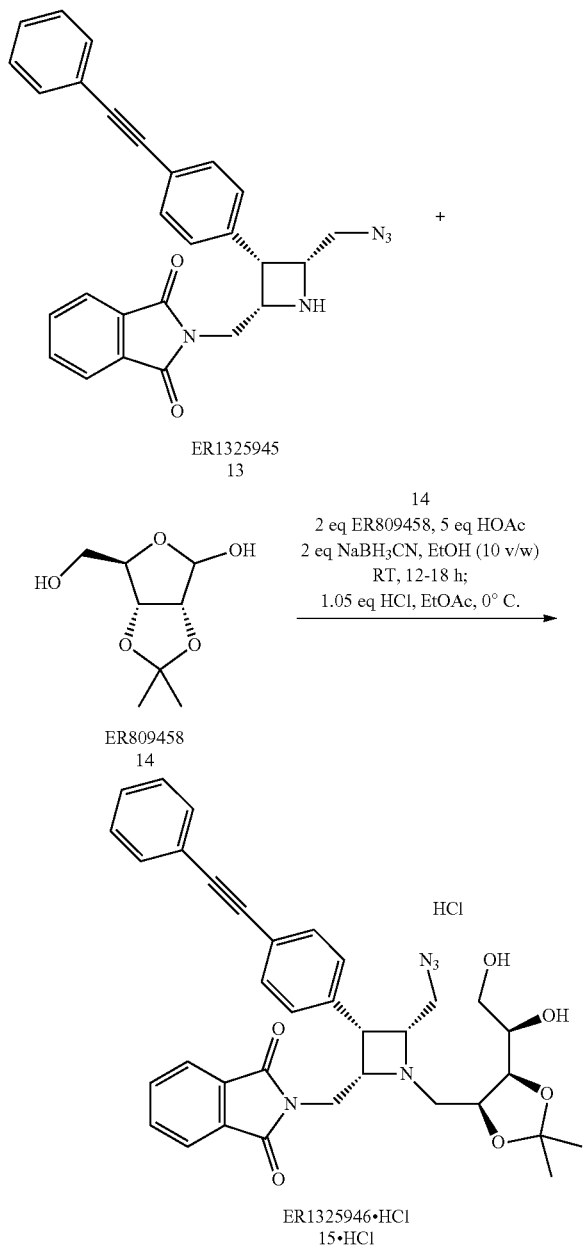

anhydrous sodium sulfate. Filter and then concentrate the organic phase using a rotary evaporator under house vacuum ($T_{bath}=37°$ C.). Take the residue into ethyl acetate (35 v/w) and filter through a plug of silica gel to remove insolubles. Cool the clear filtrate on an ice-bath,[3] slowly add a 4 M HCl-dioxane solution (0.071 v/w, 1.05 eq) over 10 minutes. Stir the white suspension on ice-bath for 10 min, then stop stirring and maintain the mixture still for 20 min to allow precipitation of the white solid.[4] Filter the mixture, firstly the clear supernatant and then the suspension of the white solid. Wash the filter cake with ethyl acetate. Dry the filter cake in a house vacuum drying oven at 40° C. to give 15.HCl (0.813 w/w, 55%) as white solid.

Expected yield (%): >55%

Maximum scale: 20 g of 12

$^1$H NMR (400 MHz, MeOH-d$_4$) δ 7.83-7.78 (m, 4H), 7.57-7.51 (m, 6H), 7.40-7.38 (m, 3H), 5.4208 (dt, J=9.7, 6.6 Hz, 1H), 4.93-4.85 (m, 1H), 4.59 (dd, 8.5, 6.5 Hz, 1H), 4.45-4.34 (m, 2H), 4.21 (dd, J=8.7, 6.4 Hz, 1H), 4.14-3.94 (m, 3H), 3.76 (d, J=9.0 Hz, 1H), 3.69-3.58 (m, 4H), 1.48 (s, 3H), 1.08 (s, 3H); $^{13}$C NMR (75 MHz, MeOH-d$_4$) δ 168.9, 135.7, 133.1, 133.1, 132.6, 132.5, 131.9, 131.8, 129.8, 129.6, 125.2, 124.4, 124.2, 111.6, 91.5, 89.2, 77.5, 74.4, 71.0, 69.2, 68.9, 65.0, 59.3, 43.7, 37.5, 28.1, 25.2

Oxidative Cleavage of 1,2-Diol 15.HCl Using Sodium Periodate

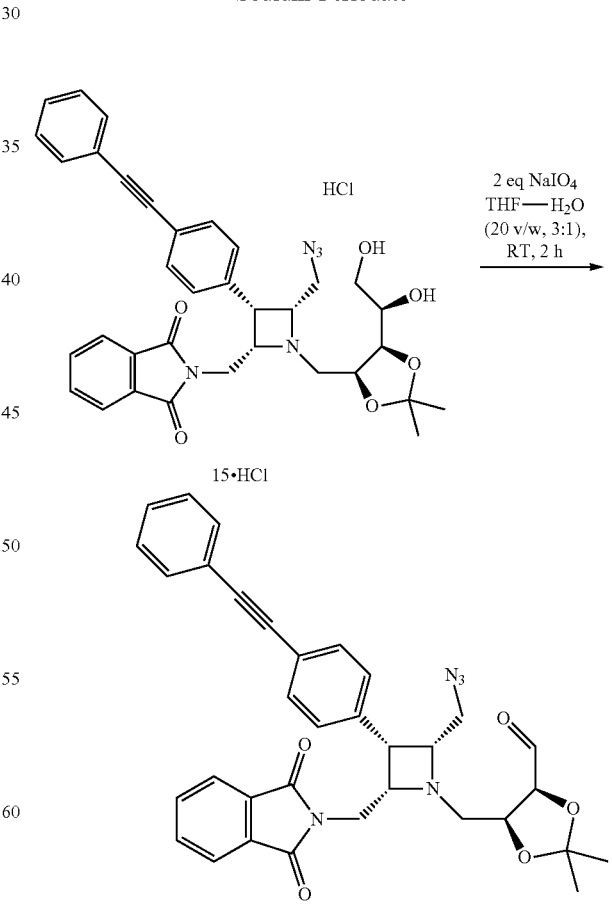

Charge a reactor with crude 13 (prepared as above, 1.0 w/w, 1.0 eq), 14 (0.850 w/w, 2.0 eq) and ethanol (10 v/w). Add to this mixture acidic acid (0.640 v/w, 0.671 w/w, 5.0 eq) and then sodium cyanoborohydride (0.281 w/w, 2.0 eq), all in one portion at room temperature.[1] Stir the mixture at room temperature for 12-18 h. Monitor for complete consumption of 13 using LCMS/UV of aliquot of the reaction. Quench the reaction using saturated aqueous sodium bicarbonate (18 v/w),[2] followed by ethyl acetate (35 v/w), and stir the mixture at room temperature for 10 minutes. Separate the two phases using a separatory vessel, back extract the aqueous phase with ethyl acetate (15 v/w) twice. Combine the organic phases, wash with brine (18 v/w) and dry with Charge a reactor with Compound 15.HCl (1.0 w/w, 1.0 eq), tetrahydrofuran (15 v/w, 13.2 w/w) and water (5 v/w, 5 w/w). Add sodium periodate (0.650 w/w, 2.0 eq) in one-portion. Stir the mixture at room temperature for 1-2 h. Monitor for complete consumption of 15 using LCMS/UV of aliquot of the reaction mixture. Pour the mixture into ethyl acetate (36 v/w, 32.4 w/w), wash with aqueous sodium bicarbonate (12 v/w) and then with 50% brine (12 v/w). Dry the organic phase over anhydrous sodium sulfate and filter. Concentrate the filtrate using a rotary evaporator under house vacuum ($T_{bath}$=37° C.) to give crude 16 (~0.9 w/w, quant.) as colorless oil.

Expected yield (%): 100%

Maximum scale: 8.3 g of 15.HCl $^1$H NMR (400 MHz, CDCl$_3$) δ 9.82 (d, J=2.8 Hz, 1H), 7.79-7.76 (m, 2H), 7.71-7.67 (m, 2H), 7.58-7.53 (m, 4H), 7.44-7.42 (m, 2H), 7.39-7.35 (m, 3H), 4.55 (dd, J=11.9, 5.8 Hz, 1H), 4.48 (dd, J=7.2, 2.8 Hz, 1H), 3.82-3.67 (m, 3H), 3.50-3.41 (m, 2H), 3.27-3.22 (m, 1H), 2.98 (dd, J=13.6, 4.7 Hz, 1H), 2.82 (dd, J=13.6, 5.7 Hz, 1H), 1.61 (s, 3H), 1.42 (s, 3H); $^{13}$C NMR (75 MHz, CDCl$_3$) δ 199.9, 167.8, 135.3, 134.0, 131.8, 131.7, 131.6, 130.6, 128.3, 128.2, 123.3, 123.2, 122.4, 110.9, 89.8, 89.2, 81.4, 66.7, 66.4, 56.9, 50.2, 44.2, 38.1, 27.3, 22.7

Tandem Staudinger/Aza-Wittig/Reduction to Convert 16 to 18.HCl

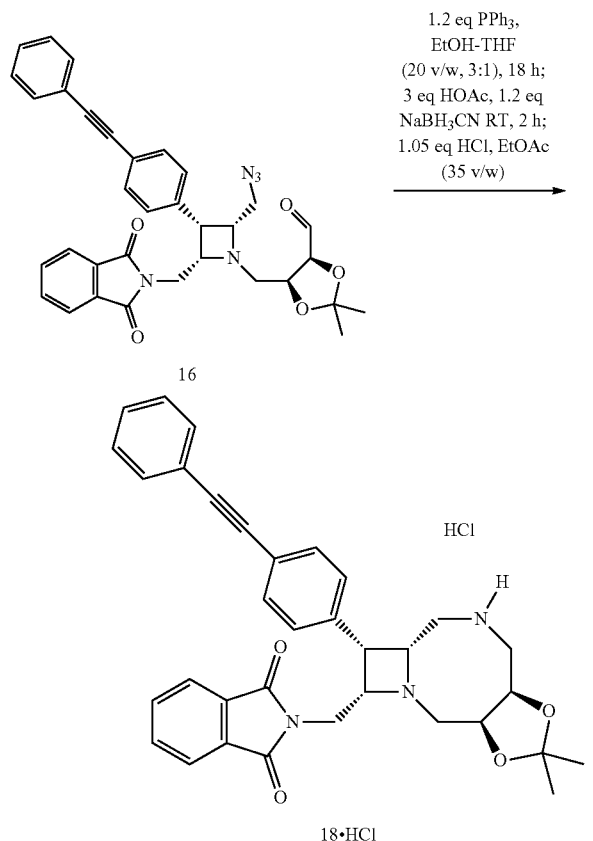 [SMILES: CC1(C)O[C@@H](CN2[C@H](CN3C(=O)c4ccccc4C3=O)[C@H](c3ccc(C#Cc4ccccc4)cc3)[C@@H]2CN=[N+]=[N-])[C@@H](C=O)O1 ; CC1(C)O[C@H]2CN3[C@H](CN4C(=O)c5ccccc5C4=O)[C@H](c4ccc(C#Cc5ccccc5)cc4)[C@@H]3CNC[C@H]2O1 ; Cl]

Charge a reactor with triphenylphosphine (0.128 w/w, 1.2 eq) and ethanol (7 v/w, 5.52 w/w). To this mixture slowly add a solution of the crude 16 (prepared as above, 1.0 w/w, 1.0 eq) in ethanol (10 v/w, 7.89 w/w) and tetrahydrofuran (5 v/w, 4.40 w/w) at room temperature over 1.5 h. Further stir the reaction mixture at room temperature for 12 h and monitor for completie consumption of 16 using LCMS/UV of aliquot of the reaction mixture. Add sodium cyanoborohydride (0.128 w/w, 1.2 eq) and acetic acid (0.291 v/w, 0.306 w/w, 3.0 eq), each in one-portion,[1] at room temperature. Stir the mixture at the temperature for 0.5-1 h and monitor for complete consumption of the imine intermediate (not shown) using LCMS/UV of aliquot of the reaction mixture. Quench the reaction with aqueous sodium bicarbonate (30 v/w) and extract with ethyl acetate (30 v/w). Further extract the aqueous phase with ethyl acetate (12 v/w) twice. Combine the organic phases, wash with brine (12 v/w) and dry over anhydrous sodium sulfate. Filter the organic phase and concentrate using a rotary evaporator under house vacuum ($T_{bath}$=37° C.). Take the residue into ethyl acetate (35 v/w) and filter to remove insolubles. Cool the solution on an ice-bath. Slowly add, with stirring, a 4 M HCl-dioxane solution (0.054 v/w, 0.065 w/w, 1.05 eq) over 10 min. Further stir the resulting white suspension on the ice-bath for 10 min, then stop stirring and keep the mixture still for 20 min to allow precipitation of the white solid.[2] Filter the mixture and wash the filter cake with ethyl acetate. Dry the filter cake in a house vacuum drying oven at 40° C. to give 18.HCl (0.81 w/w, 82%) as white solid.

Expected yield (%): 80%

Maximum scale: 8.3 g of 18.HCl

1) Additional Spectral Data

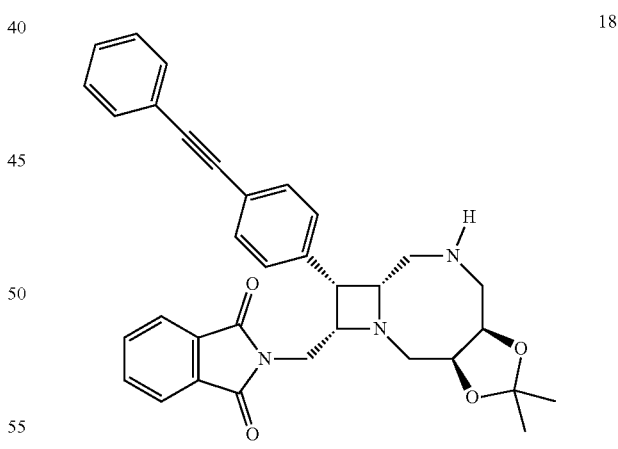

Compound 18: $^1$H NMR (400 MHz, CDCl$_3$) δ 7.82-7.78 (m, 2H), 7.71-7.65 (m, 2H), 7.55-7.49 (m, 6H), 7.38-7.31 (m, 3H), 4.40-4.35 (m, 1H), 4.23-4.19 (m, 1H), 3.79 (dd, J=14.2, 5.5 Hz, 1H), 3.70 (dd, J=11.7, 6.0 Hz, 1H), 3.51 (dd, J=14.2, 5.2 Hz, 1H), 3.28 (dd, J=14.6, 8.5 Hz, 1H), 3.09 (dd, J=14.6, 2.4 Hz, 1H), 2.87-2.68 (m, 3H), 2.59 (brd, J=13.3 Hz, 1H), 1.74 (brs, 1H), 1.39 (s, 3H), 1.33 (s, 3H); $^{13}$C NMR (75 MHz, CDCl$_3$) δ 167.9, 136.6, 133.9, 131.9, 131.5, 131.2, 130.8, 128.3, 128.1, 123.3, 123.2, 121.8, 106.8, 89.5, 89.3, 77.7, 68.2, 65.1, 57.7, 48.7, 45.5, 44.7, 38.5, 27.8, 25.1

21

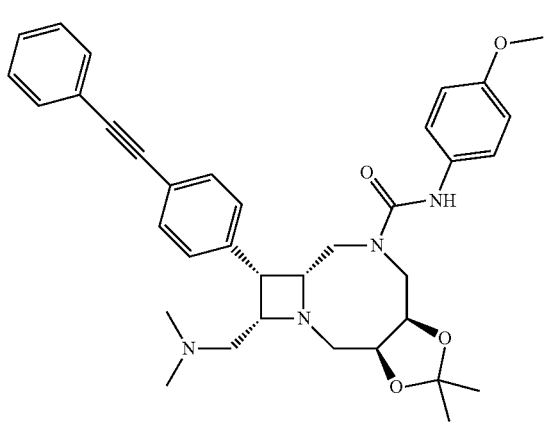

Compound 21: ¹H NMR (400 MHz, CDCl$_3$) δ 8.32 (brs, 1H), 7.56-7.53 (m, 2H), 7.52-7.50 (m, 2H), 7.45-7.43 (m, 2H), 7.39-7.33 (m, 3H), 7.25-7.21 (m, 2H), 6.85-6.82 (m, 2H), 4.36 (dd, J=16.8, 2.7 Hz, 1H), 4.30-4.28 (m, 1H), 4.23-4.18 (m, 1H), 4.13-4.09 (m, 1H), 3.78 (s, 3H), 3.69-3.65 (m, 1H), 3.63-3.54 (m, 3H), 2.79 (brd, J=8.0 Hz, 2H), 2.63 (dd, J=13.7, 10.5 Hz, 1H), 2.44 (dd, J=13.3, 8.2 Hz, 1H), 2.34 (dd, J=13.1, 3.7 Hz, 1H), 2.05 (s, 6H), 1.52 (s, 3H), 1.44 (s, 3H); ¹³C NMR (75 MHz, CDCl$_3$) δ 156.9, 155.2, 136.9, 133.1, 131.5, 131.1, 130.7, 128.3, 128.2, 123.2, 121.6, 121.0, 114.1, 107.7, 89.6, 89.1, 78.2, 77.0, 68.2, 66.2, 57.9, 57.4, 55.5, 51.5, 45.6, 44.7, 28.4, 26.1

Although embodiments of the present invention have been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims

What is claimed is:

1. A method of forming a solid compound given by Formula I:

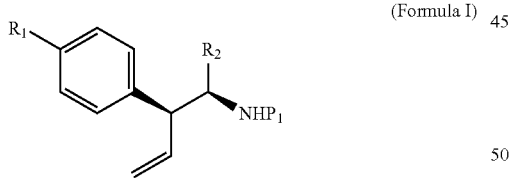

wherein:
$R_1$ is —I, —Cl, —Br, or

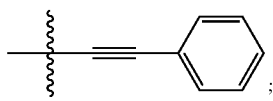

$R_2$ is C(O)$R_3$;
wherein $R_3$ is —O⁻ and a positive counterion ionically associated with Formula I;
$P_1$ is a nitrogen protecting group;
wherein the method comprises reacting a reactant of Formula II

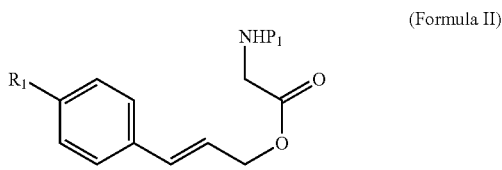

with a base and resolving the racemic mixture by crystallization with a chiral reagent.

2. The method according to claim 1, wherein $R_1$ is

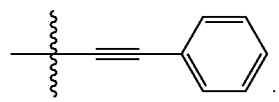

3. The method according to claim 2, wherein $P_1$ is selected from the group consisting of
—C(O)CF$_3$, —C(O)OC(CH$_3$)$_3$, and —C(O)OCH$_2$Ph.

4. The method according to claim 3, wherein $P_1$ is —C(O)CF$_3$.

5. The method of claim 4, wherein the base is lithium diisopropyl amine and the reacting step occurs in the presence of ZnCl$_2$.

6. The method of claim 5, wherein the chiral reagent is (R)-(+)-1-phenylethylamine.

7. A method of forming a compound given by Formula I:

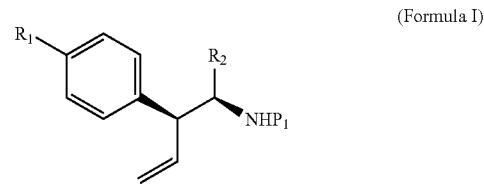

wherein:
$R_1$ is —I, —Cl, —Br, or

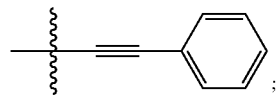

$R_2$ is C(O)$R_3$;
wherein $R_3$ is —Oalkyl;
$P_1$ is a nitrogen protecting group;
wherein the method comprising reacting a reactant of Formula III

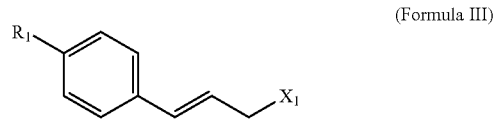

with a chiral sulfinyl imine;
wherein $X_1$ is a halogen atom.

8. The method according to claim 7, wherein

R₁ and X₁ are each —Br, and the chiral sulfinyl imine is

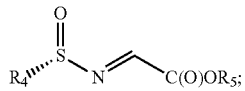

wherein R₄ and R₅ are a linear or branched alkyl.

9. The method of claim 8, wherein R₄ is —C(CH₃)₃ and R₅ is —CH₂CH₃.

10. The method of claim 9, wherein the reacting step occurs in the presence of Zn.

11. A method of forming a compound given by Formula IV

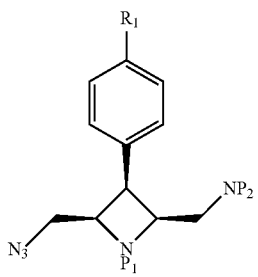

wherein R₁ is —I, —Cl, —Br, or

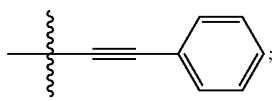 [SMILES: *C#Cc1ccccc1]

P₁ and P₂ are the same or different and represent nitrogen protecting groups;

wherein the method comprises:

(i) forming a lactone of Formula V

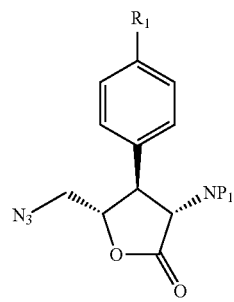

from a compound or Formula 1

wherein R₂ is C(O) R₃;

wherein R₃ is —OH, —Oalkyl, —O⁻;

wherein when R₃ is —O⁻, a positive counterion is ionically associated with Formula I;

and P₁ is a nitrogen protecting group;

(ii) reducing said lactone of Formula V into a compound of Formula VI

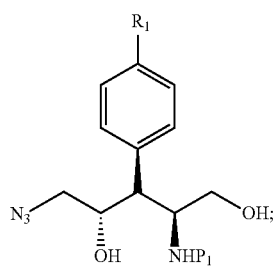

and (iii) converting the alcoholic groups covalently attached to the unsaturated carbons of Formula VI into leaving groups to form an intermediate that reacts with a nitrogen nucleophile to generate a compound of Formula IV.

12. The method of claim 11, wherein said nitrogen nucleophile is phthalimide.

13. The method of claim 12, wherein R₁ is

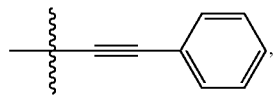 [SMILES: *C#Cc1ccccc1]

R₂ is —C(O)O⁻, and P₁ is —C(O)CF₃.

14. The method of claim 13, wherein said lactone of Formula V is formed by reacting the compound of Formula I with an electropositive source of a halogen in a polar solvent.

15. The method of claim 14, wherein said electropositive source of a halogen is I₂ and said polar solvent is an aqueous mixture of CH₃CN.

16. The method of claim 13, wherein said lactone of Formula V is formed by reacting the compound of Formula I with I₂ in a polar solvent to form a first product, and reacting the first product with NaN₃ to form a compound of Formula V.

17. The method of claim 16, wherein the reducing step occurs in the presence of NaBH₄.

18. The method of claim 17, wherein said leaving groups are mesylate groups and said intermediate is given by one or both of the following structures:

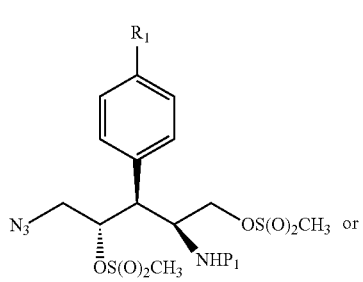
(Formula VII)

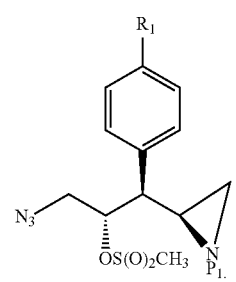
(Formula VIIb)

19. The method of claim 18, wherein $P_1$ is converted from —C(O)CF$_3$ into the following structure:

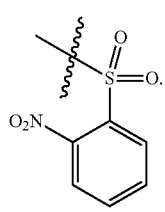

20. The method of claim 11, wherein $R_1$ is —Br, $R_2$ is —C(O)OCH$_2$CH$_3$ and $P_1$ is —S(O)C(CH$_3$)$_3$.

21. The method of claim 20, wherein $P_1$ is converted from —S(O)C(CH$_3$)$_3$ to a structure as follows:

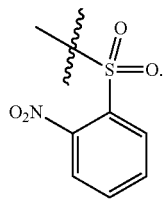

22. The method of claim 21, wherein said lactone of Formula V is formed by reacting the compound of Formula I with an electropositive source of a halide in a polar solvent to form a first product, and reacting the first product with NaN$_3$ to form a compound of Formula V.

23. The method of claim 22, wherein said lactone of Formula V is reduced with NaBH$_4$ to form the following compound:

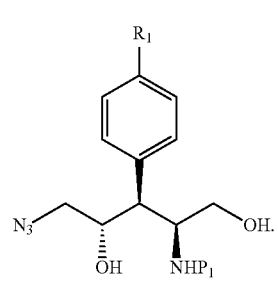
(Formula VI)

24. The method of claim 23, wherein said leaving groups are mesylate groups and said intermediate is given by one or both of the following structures:

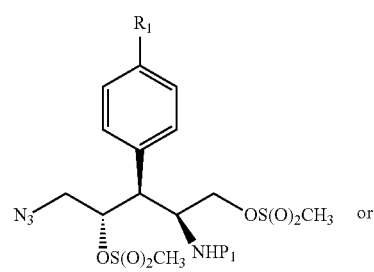
(Formula VII)

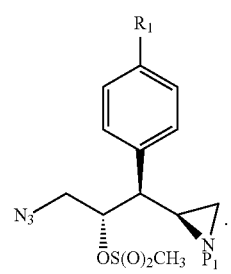
(Formula VIIb)

25. A method of making a compound given by the following structure

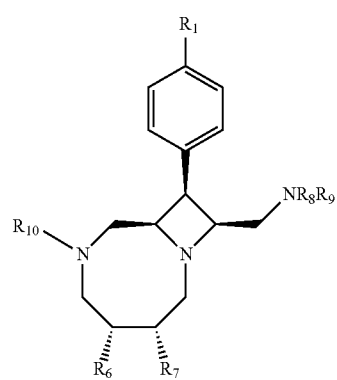
(Formula VIII)

wherein:

$R_1$ is —I, —Cl, —Br, or

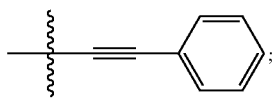

$R_6$ and $R_7$ are independently the same or different, and are selected from —H, —OH, alkyl, —Oalkyl, or wherein $R_6$ and $R_7$ together with the atoms to which they are attached form a ring system protecting group for a diol;

$R_8$ and $R_9$ are independently the same or different, and are selected from —H, -alkyl, —C(O)alkyl, —S(O)$_2$alkyl, or $R_8$ and $R_9$ together with the N to which they are attached form:

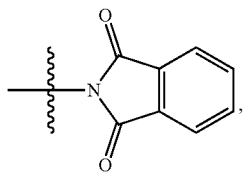 [SMILES: *N1C(=O)c2ccccc2C1=O]

or a nitrogen protecting group;

$R_{10}$ is —H, a straight chain or branched alkyl, —C(O) alkyl, —C(O)O-alkyl, —C(O)NH-alkyl, —C(O) aryl, —C(O)O-aryl, —C(O)NH-aryl, —C(O) heteroaryl, —C(O)O-heteroaryl, and —C(O)N-heteroaryl;

wherein said aryl is a phenyl group optionally substituted with 1-3 groups of —OCH$_3$, —OH, and halogen; and said heteroaryl is selected from the group consisting of triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, oxetanyl, azepinyl, piperazinyl, morpholinyl, dioxanyl, thietanyl and oxazolyl;

wherein the method comprises reacting a compound given by Formula IV

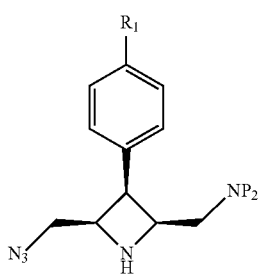

(Formula IV)

with a substituted γ-hydroxyaldehyde to promote bicyclization.

26. The method according to claim 25, wherein said γ-hydroxyaldehyde is given by the following structure:

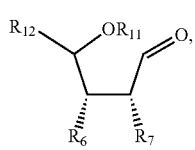

(Formula IX)

wherein $R_{11}$ is —H or an oxygen protecting group; and $R_{12}$ is —H or —CH$_2$OH.

27. The method according to claim 26, wherein said γ-hydroxyaldehyde is

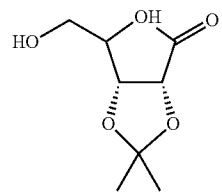

and the compound of Formula VIII is made proceeding through the following intermediate:

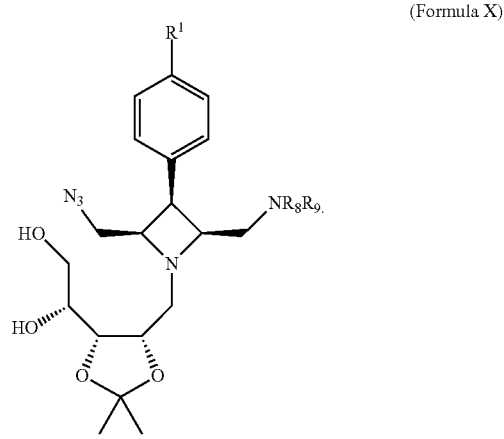

(Formula X)

28. The method according to claim 27, wherein the method further comprises an oxidation of Formula X to produce the following intermediate for the production of the compound of Formula VIII:

(Formula XI)

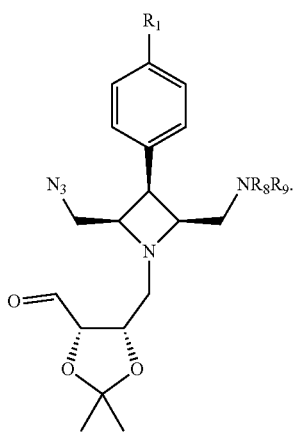

29. The method according to claim 28, wherein the method further comprises a reduction and bicyclization of Formula XI to produce the following intermediate for the production of the compound of Formula VIII:

(Formula XII)

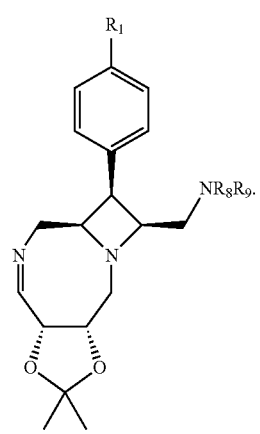

30. The method according to claim 29, wherein the method further comprises reducing the compound of Formula XII to produce the following intermediate for the production of the compound of Formula VIII:

(Formula XIII)

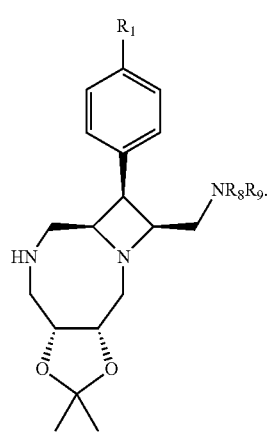

31. The method according to claim 30, wherein the compound of Formula XIII reacts with 4-methoxyphenyl isocyanate to produce the following intermediate for the production of the compound of Formula VIII:

(Formula XIV)

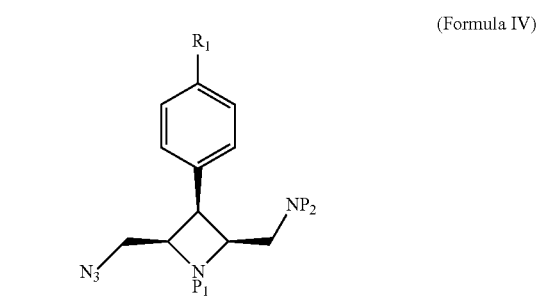

32. A method of forming a compound given by Formula IV (Formula IV)

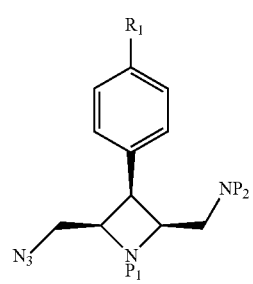

wherein:

$R_1$ is —I, —Cl, —Br, or

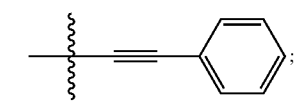

$P_1$ and $P_2$ are the same or different and represent nitrogen protecting groups;

wherein the method comprises converting the alcoholic groups covalently attached to the unsaturated carbons of Formula VI (Formula VI)

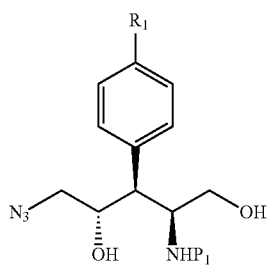

into leaving groups to form an intermediate that reacts with a nitrogen nucleophile to generate a compound of Formula IV.

33. The method according to claim 32, wherein said leaving groups are mesylate groups and said intermediate is given by one or both of the following structures:

(Formula VII)

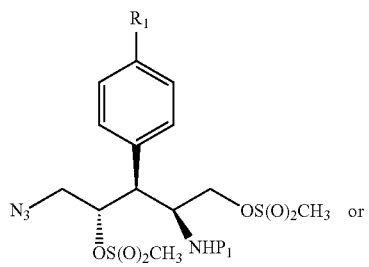

(Formula VIIb)

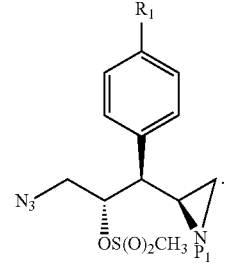

34. The method according to claim 33, wherein said nitrogen nucleophile is phthalimide.

35. A compound or a pharmaceutically acceptable salt thereof of Formula XV:

(Formula XV)

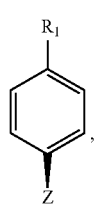

wherein $R_1$ is —I, —Cl, —Br, or and

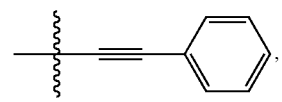

and wherein Z is a substituted 4-membered nitrogen-containing heterocycle selected from the group consisting of:

(i)

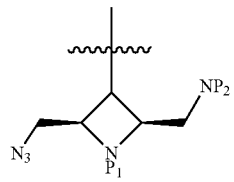

wherein $P_1$ and $P_2$ are the same or different and are nitrogen protecting groups or —H, or a pharmaceutically acceptable salt thereof;

(ii)

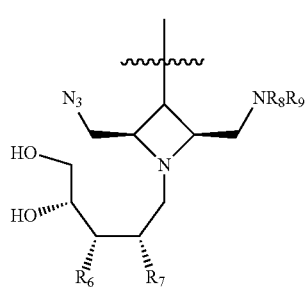

wherein $R_8$ and $R_9$ are independently the same or different, and are selected from —H, -alkyl, —C(O)alkyl, —S(O)$_2$alkyl, or $R_8$ and $R_9$ together with the N to which they are attached form:

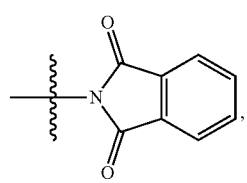 [SMILES: *N1C(=O)c2ccccc2C1=O]

or a nitrogen protecting group,
wherein the alkyl is substituted by one or more halogens; or a pharmaceutically acceptable salt thereof;

(iv)
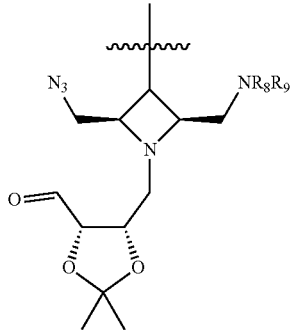

wherein $R_8$ and $R_9$ are independently the same or different, and are selected from —H, -alkyl, —C(O)alkyl, —S(O)$_2$alkyl, or $R_8$ and $R_9$ together with the N to which they are attached form:

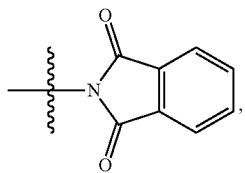 [SMILES: *N1C(=O)c2ccccc2C1=O]

or a nitrogen protecting group,
wherein the alkyl is substituted by one or more halogens; or a pharmaceutically acceptable salt thereof;

(v)
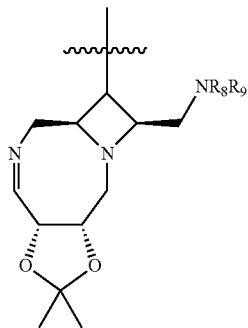

wherein $R_8$ and $R_9$ are independently the same or different, and are selected from —H, -alkyl, —C(O)alkyl, —S(O)$_2$alkyl, or $R_8$ and $R_9$ together with the N to which they are attached form;

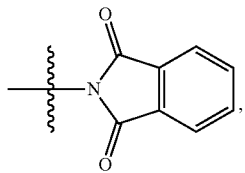 [SMILES: *N1C(=O)c2ccccc2C1=O]

or a nitrogen protecting group,
wherein the alkyl is substituted by one or more halogens; or a pharmaceutically acceptable salt thereof; and (vi)
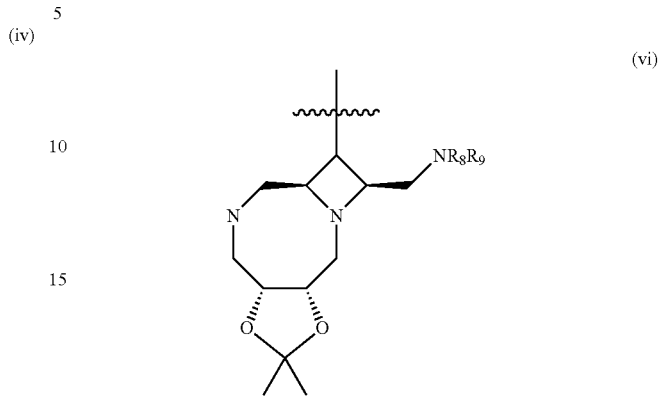

wherein $R_8$ and $R_9$ are independently the same or different, and are selected from —H, —C(O)alkyl, —S(O)$_2$alkyl, or $R_8$ and $R_9$ together with the N to which they are attached form;

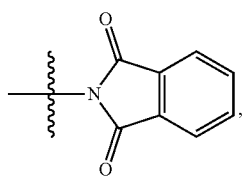 [SMILES: *N1C(=O)c2ccccc2C1=O]

or a nitrogen protecting group,
wherein the alkyl is optionally substituted by one or more halogens; or a pharmaceutically acceptable salt thereof.

36. The compound or pharmaceutically acceptable salt of claim 35, wherein the compound is compound of Formula IV:

(iii)
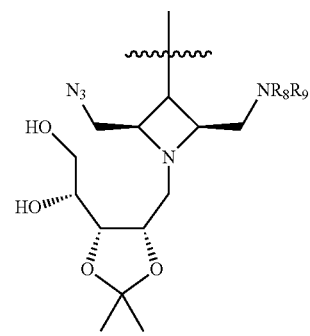

wherein R₁ is —I, —Cl, —Br,

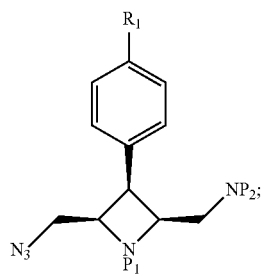
(Formula IV)

and
P₁ and P₂ are the same or different and are nitrogen protecting groups or —H;
or a pharmaceutically acceptable salt thereof.

37. The compound or pharmaceutically acceptable salt of claim 35, wherein said compound is a compound of Formula X:

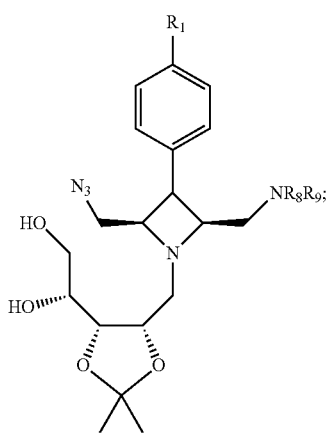
(Formula X)

wherein $R^1$ is —I, —Cl, —Br, or

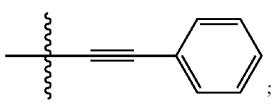
;

and
R₈ and R₉ are independently the same or different, and are selected from —H, -alkyl, —C(O)alkyl, —S(O)₂alkyl, or R₈ and R₉ together with the N to which they are attached form

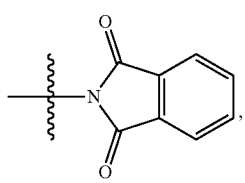 [SMILES: *N1C(=O)c2ccccc2C1=O]
, or a nitrogen protecting group,
wherein the alkyl is substituted by one or more halogens, hydrogen;
or a pharmaceutically acceptable salt thereof.

38. The compound or pharmaceutically acceptable salt of claim 35, wherein the compound is a compound of Formula XI:

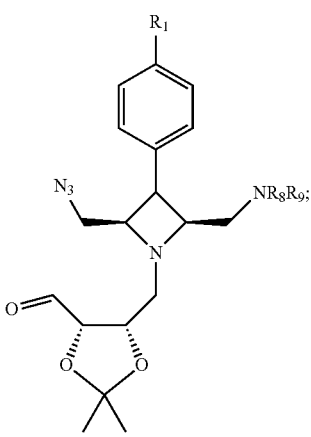
(Formula XI)

wherein R₁ is —I, —Cl, —Br, or

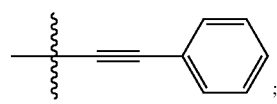
;

and
R₈ and R₉ are independently the same or different, and are selected from —H, -alkyl, —C(O) alkyl, —S(O)₂alkyl, or R₈ and R₉ together with the N to which they are attached form

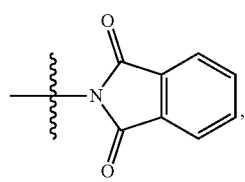 [SMILES: *N1C(=O)c2ccccc2C1=O]
, or a nitrogen protecting group,
wherein the alkyl is substituted by one or more halogens;
or a pharmaceutically acceptable salt thereof.

39. The compound or pharmaceutically acceptable salt of claim 35, wherein the compound is a compound of Formula XII:

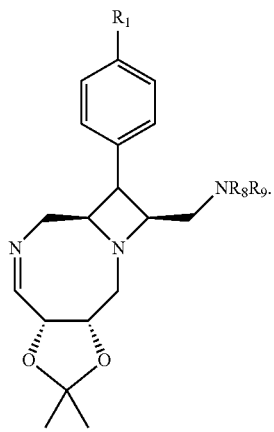

(Formula XII)

wherein in Formula XII, $R_1$ is —I, —Cl, —Br, or

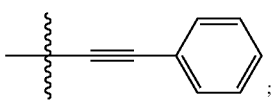

;

and $R_8$ and $R_9$ are independently the same or different, and are selected from —H, -alkyl, —C(O)alkyl, —S(O)$_2$alkyl, or $R_8$ and $R_9$ together with the N to which they are attached form:

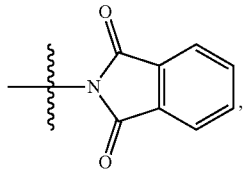 [SMILES: *N1C(=O)c2ccccc2C1=O]

, or a nitrogen protecting group,
wherein the alkyl is substituted by one or more halogens;
or a pharmaceutically acceptable salt thereof.

40. The compound or pharmaceutically acceptable salt of claim 35,
wherein the compound is a compound of Formula XIII:

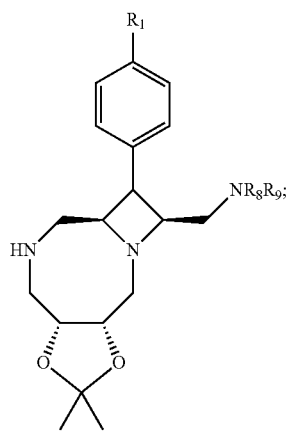

(Formula XIII)

wherein $R_1$ is —I, —Cl, —Br, or

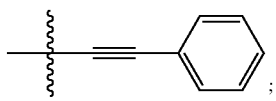

;

and $R_8$ and $R_9$ are independently the same or different, and are selected from —H, —C(O) alkyl, —S(O)$_2$alkyl, or $R_8$ and $R_9$ together with the N to which they are attached form

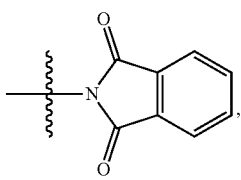 [SMILES: *N1C(=O)c2ccccc2C1=O]

, or a nitrogen protecting group,
wherein the alkyl is optionally substituted by one or more halogens;
or a pharmaceutically acceptable salt thereof.

41. A compound or pharmaceutically acceptable salt thereof wherein the compound has Formula XV:

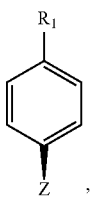

(Formula XV)

wherein R₁ is —I, —Cl, —Br, or

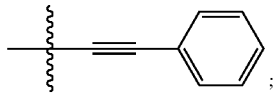;

wherein Z is selected from the group consisting of:

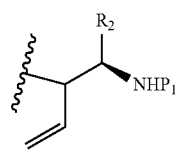 (i)

wherein R₂ is C(O) R₃;
R₃ is —O⁻ and a positive counterion ionically associated with Formula XVI, or R₃ is —OH; and
P₁ is a nitrogen protecting group or —H;

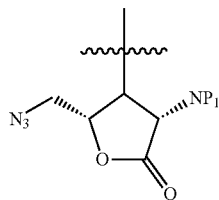 (ii)

wherein P₁ is a nitrogen protecting group or —H;

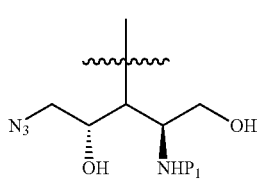 (iii)

wherein P₁ is a nitrogen protecting group or —H;

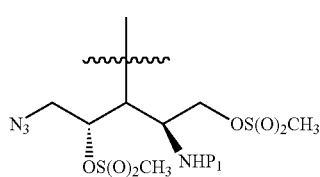 (iv)

wherein P₁ is a nitrogen protecting group or —H; and

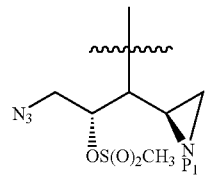 (v)

wherein P₁ is a nitrogen protecting group or —H;
or a pharmaceutically acceptable salt thereof.

42. The compound or pharmaceutically acceptable salt of claim 41, wherein the compound is a compound of Formula I:

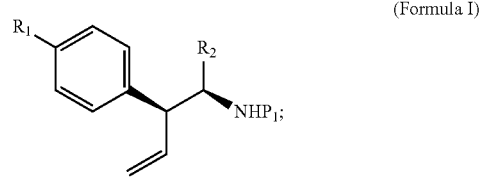 (Formula I)

wherein R₁ is

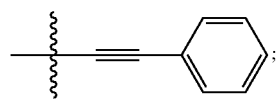 [SMILES: *C#Cc1ccccc1];

R₂ is C(O)R₃;
R₃ is —O⁻ and a positive counterion ionically associated with Formula I, or R₃ is —OH; and P₁ is a nitrogen protecting group or —H;
or a pharmaceutically acceptable salt thereof.

43. The compound or pharmaceutically acceptable salt of claim 41, wherein the compound is a compound of Formula V:

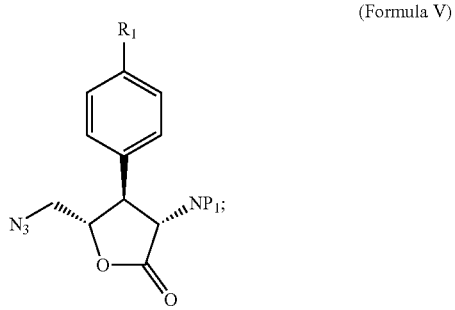 (Formula V)

wherein R₁ is —I, —Cl, —Br, or

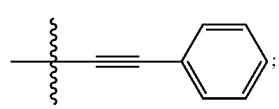 [SMILES: *C#Cc1ccccc1];

and P₁ is a nitrogen protecting group or —H;
or a pharmaceutically acceptable salt thereof.

44. The compound or pharmaceutically acceptable salt of claim 41, wherein the compound is a compound of Formula VI:

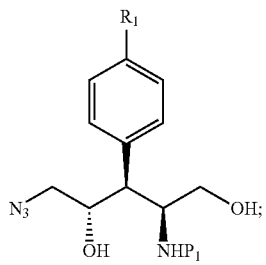
(Formula VI)

wherein $R_1$ is —I, —Cl, —Br, or

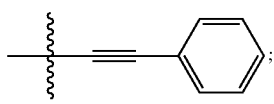 [SMILES: *C#Cc1ccccc1]

and $P_1$ is a nitrogen protecting group or —H;
or a pharmaceutically acceptable salt thereof.

45. The compound or pharmaceutically acceptable salt of claim 41, wherein the compound is a compound of Formula VII:

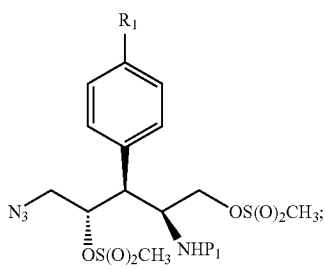
(Formula VII)

wherein $R_1$ is —I, —Cl, —Br, or

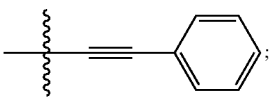 [SMILES: *C#Cc1ccccc1]

$P_1$ is a nitrogen protecting group or —H;
or a pharmaceutically acceptable salt thereof.

46. The compound or pharmaceutically acceptable salt of claim 41, wherein the compound is a compound of Formula VIIb:

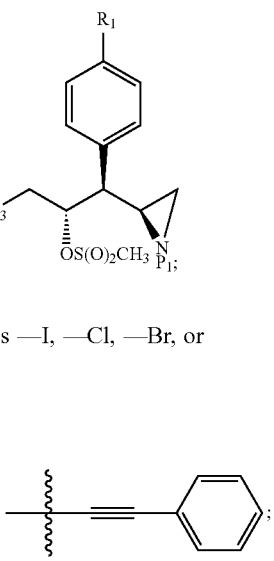
(Formula VIIb)

wherein $R_1$ is —I, —Cl, —Br, or

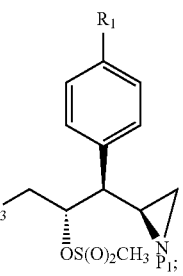

and
$P_1$ is a nitrogen protecting group or —H;
or a pharmaceutically acceptable salt thereof.

* * * * *